US009327003B2

(12) United States Patent
Drapeau et al.

(10) Patent No.: US 9,327,003 B2
(45) Date of Patent: May 3, 2016

(54) USE OF FOTI TO ENHANCE STEM CELL MOBILIZATION AND PROLIFERATION

(71) Applicant: Stemtech International, Inc., San Clemente, CA (US)

(72) Inventors: Christian Drapeau, San Clemente, CA (US); Gitte S. Jensen, Port Dover (CA)

(73) Assignee: STEMTECH INTERNATIONAL, INC., Pembroke Pines, FL (US)

( * ) Notice: Subject to any disclaimer, the term of this patent is extended or adjusted under 35 U.S.C. 154(b) by 43 days.

(21) Appl. No.: 14/357,620

(22) PCT Filed: Nov. 15, 2012

(86) PCT No.: PCT/US2012/065294
§ 371 (c)(1),
(2) Date: May 12, 2014

(87) PCT Pub. No.: WO2013/074801
PCT Pub. Date: May 23, 2013

(65) Prior Publication Data
US 2014/0342010 A1    Nov. 20, 2014

Related U.S. Application Data

(60) Provisional application No. 61/561,431, filed on Nov. 18, 2011.

(51) Int. Cl.
| | | |
|---|---|---|
| A01N 65/00 | (2009.01) | |
| A61K 36/704 | (2006.01) | |
| A61K 36/815 | (2006.01) | |
| A61K 31/737 | (2006.01) | |
| A61K 35/20 | (2006.01) | |
| A61K 35/748 | (2015.01) | |
| A61K 36/05 | (2006.01) | |
| A61K 36/068 | (2006.01) | |
| A61K 36/07 | (2006.01) | |
| A61K 36/074 | (2006.01) | |
| A61K 9/48 | (2006.01) | |
| A61K 36/03 | (2006.01) | |

(52) U.S. Cl.
CPC ............ *A61K 36/704* (2013.01); *A61K 9/48* (2013.01); *A61K 31/737* (2013.01); *A61K 35/20* (2013.01); *A61K 35/748* (2013.01); *A61K 36/03* (2013.01); *A61K 36/05* (2013.01); *A61K 36/068* (2013.01); *A61K 36/07* (2013.01); *A61K 36/074* (2013.01); *A61K 36/815* (2013.01); *A61K 2236/33* (2013.01)

(58) Field of Classification Search
CPC ..................................................... A61K 36/00
USPC ........................................................ 424/725
See application file for complete search history.

(56) References Cited

U.S. PATENT DOCUMENTS

| 7,939,057 B2 | 5/2011 | Battista et al. |
|---|---|---|
| 2005/0042314 A1 | 2/2005 | Wu |
| 2006/0068022 A1 | 3/2006 | Playford |
| 2007/0003669 A1 | 1/2007 | Kearl et al. |
| 2007/0020358 A1 | 1/2007 | Mower |
| 2007/0122492 A1 | 5/2007 | Behr et al. |
| 2007/0190023 A1 | 8/2007 | Battista et al. |
| 2008/0085322 A1 | 4/2008 | Xu |
| 2008/0089941 A1 | 4/2008 | Mower |
| 2008/0138321 A1 | 6/2008 | Jensen et al. |
| 2008/0171720 A1 | 7/2008 | Garssen et al. |
| 2008/0247989 A1 | 10/2008 | Shih et al. |
| 2009/0074896 A1 | 3/2009 | Wu |
| 2009/0274720 A1 | 11/2009 | Zhuang et al. |
| 2010/0144667 A1 | 6/2010 | Shaklee et al. |
| 2010/0173024 A1 | 7/2010 | McDaniel |
| 2011/0287061 A1 | 11/2011 | Beggan |
| 2012/0282194 A1 | 11/2012 | Florence |
| 2013/0108587 A1 | 5/2013 | Drapeau et al. |
| 2014/0342010 A1 | 11/2014 | Drapeau et al. |

FOREIGN PATENT DOCUMENTS

| AU | 2011276479 B2 | 10/2015 |
|---|---|---|
| CN | 101433313 A | 5/2009 |
| EP | 2588119 | 5/2013 |
| JP | 2878597 B2 | 4/1999 |
| JP | 2003-135028 A | 5/2003 |

(Continued)

OTHER PUBLICATIONS

Kiss et al. Enhancement of Organ Regeneration in Animal Models, by a Stem Cell-Stimulating Plant Mixture. Journal of Medicinal Food (2010). 13(3):599-604.

No author Why Colostem? Colstem-colostrum—60 capsules. Retrieved from <http://www.immune.co.nz/product_info.php/products_id/20> 2 pages.

No author. Talking about Zradical Juice has Acai Berry, Manosteen Other Healthy Ingredients. (2009). Retrieved from <https://escapeyoung.wordpress.com/2009/11/05/talking-about-zradical-juice-has-acai-berry-mangosteem-other-healthy-ingredients> 2 pages.

(Continued)

*Primary Examiner* — Michael Meller
(74) *Attorney, Agent, or Firm* — Stephen W. Chen; Nixon Peabody LLP

(57) ABSTRACT

The present invention provides a method of using *Polygonum multiflorum* or extracts thereof to enhance stem cell mobilization in a subject, including hematopoietic stem cells (HSCs) and bone marrow stem cells (BM-SCs). In one embodiment, a blended composition of plant parts, fruits, mushrooms, microorganisms, maternal fluids, and extracts thereof are used to promote mobilization of stem cells, resulting in migration of the stem cells to specific sties of maintenance and repair within tissues and/or organs. Increased circulation of HSCs and/or BMSCs and migration towards sites of maintenance promotes the natural regeneration mechanisms in the body.

9 Claims, 12 Drawing Sheets

(56) References Cited

FOREIGN PATENT DOCUMENTS

| JP | 2003-259844 | A  | 9/2003  |
|----|-------------|----|---------|
| JP | 2009-221133 | A  | 10/2009 |
| KR | 20080007698 | A  | 1/2008  |
| WO | 2007002570  | A1 | 1/2007  |
| WO | 2012006100  | A2 | 1/2012  |
| WO | 2013022788  | A1 | 2/2013  |
| WO | 2013074801  | A1 | 5/2013  |
| WO | 2013101713  | A1 | 7/2013  |
| WO | 2014011752  | A1 | 1/2014  |
| WO | 2014205250  | A1 | 12/2014 |
| ZA | 2013/00101  |    | 3/2014  |

OTHER PUBLICATIONS

Unknown Author. Komplex hatasu keszitmeny, es eijaras a veraramba kerulo ossejtek szamanak fokozasara, as ossejtek vedelmere, a p53 gen expressziojanak fokozasara. Hungarian Patent Invention No. 0700594 (HU 2007000594 A2); 8 pages.

Ember et al. Can we increase CD34+ stem cell numbers in circulating peripheral blood using natural compounds in animals? Anticancer Research (2008). 28: 3274-3275. Abstract Only.

Chen et al. Medicine and its preparation method for treating Parkinsons disease—made from deeply fermenting Cordyceps and can improve patients ability in tissue metabolism and immunity of body organs so as to achieve complete cure effect. Taiwanese Publication TW 201041586. (2011). Abstract Only.

Szabo. Pharmaceutical preparation comprises dried and ground material including hemp seed, shark cartilage, Ganoderma lucidum and boxthom fruit, and chlorophyll, dried maize grains, blue-green algae and gelatin or titanium dioxide. XP-002716327 (2009). 3 pages. Abstract Only.

PC/US2011/042211 International Search Report and Written Opinion dated Jan. 9, 2012.

English translation of Abstract only for CN 101433313A. XP-002738625.

PCT/US2011/042211 International Preliminary Report on Patentability dated Dec. 28, 2012.

PCT/US2012/065294 International Search Report and Written Opinion dated Feb. 1, 2013.

Irhimeh et al. Fucoidan ingestion increases the expresseion of CXCR4 on human CD34+ cells. Experimental Hematology (2007). 35:989-994.

PCT/US2013/049697 International Search Report and Written Opinion dated Nov. 22, 2013.

Koh, Jong-Ho; et al: "Activation of Macrophages and the Intestinal Immune System by an Orally Administered Decoction from Cultured Mycelia of Cordyreps sinensis" Bioscience, Biotechnology and Biochemistry, 66, 407-411, 2002.

Wang, Yuan-Yuan; et al; "Studies on the Immune-Modulating and Antitumor Activities of Ganoderma lucidum (Reishi) Polysaccharides: Functional and Proteomic Analyses of a Fucose-Contairling Glycoprotein Fraction Responsible for the Activities," Bioorganic & Medicinal Chemistry, 10, 1057-1062, 2002.

Sweeney, Elizabeth A.; et al: "Sulfated polysaccharides increase plasma levels of SDf-1 in monkeys and ice: involvement in mobilization of stem/progenitor cells," Blood. 99, 44-51, 2002.

International Search Report and Written Opinion dated Feb. 4, 2015 for International application No. PCT/US14/67734.

International Preliminary Report on Patentability dated May 20, 2014 for International application No. PCT/US2012/065294.

International Search Report and Written Opinion dated Oct. 23, 2014 for International application No. PCT/US14/43237

Razafison, Rivonala, The 'remedy of legend', African Review, Jan. 28, 2011 [online]. Retrieved from the Internet: <http://www.africareview.com/Special-Reports/-/979182/1097226/-/xmdfyyz/-/index.html>.

International Preliminary Report on Patentability dated Jan. 13, 2015 for International application No. PCT/US2013/049897.

Figure 1.
A.
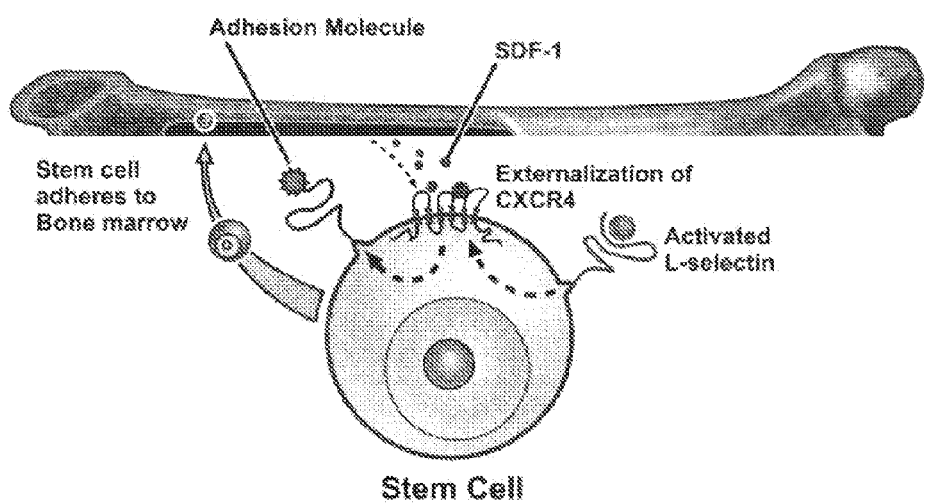
B.
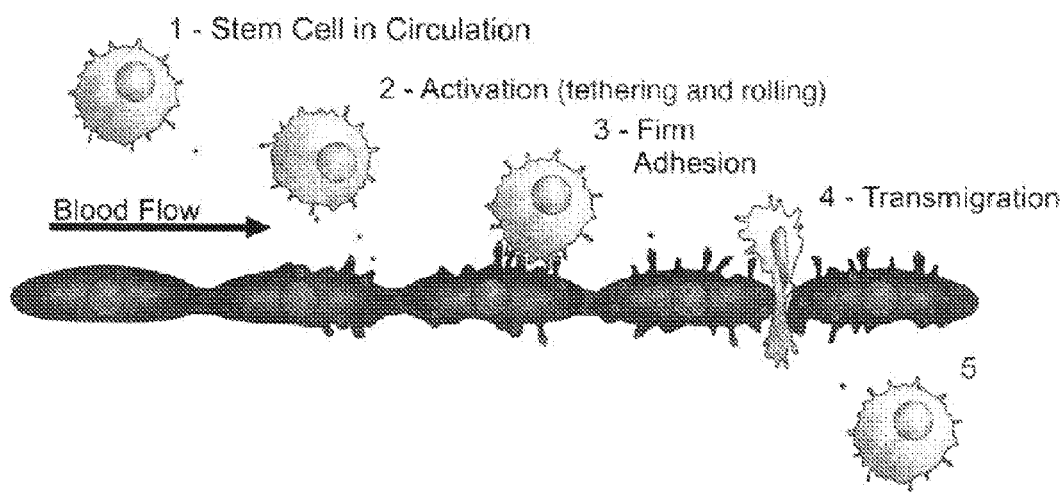

C.

Figure 3.
A.
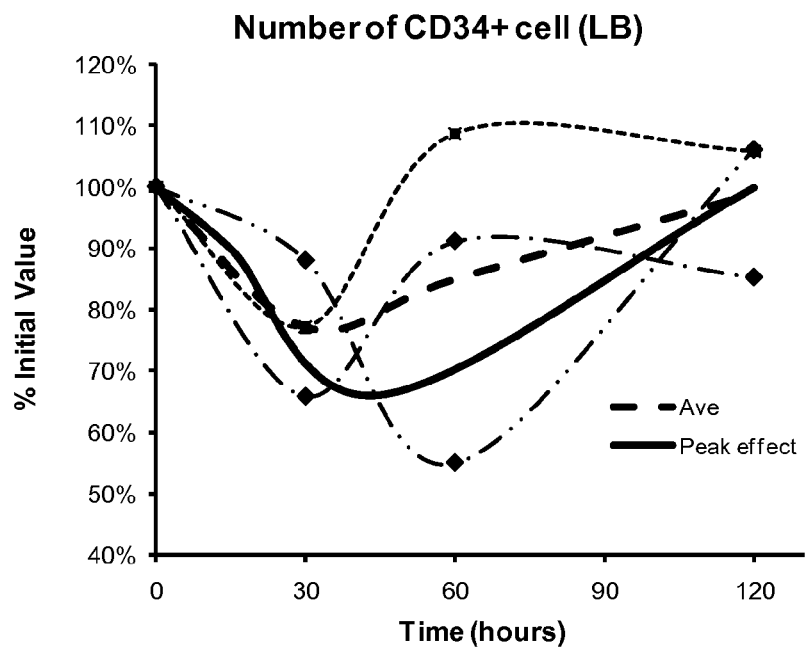
B.
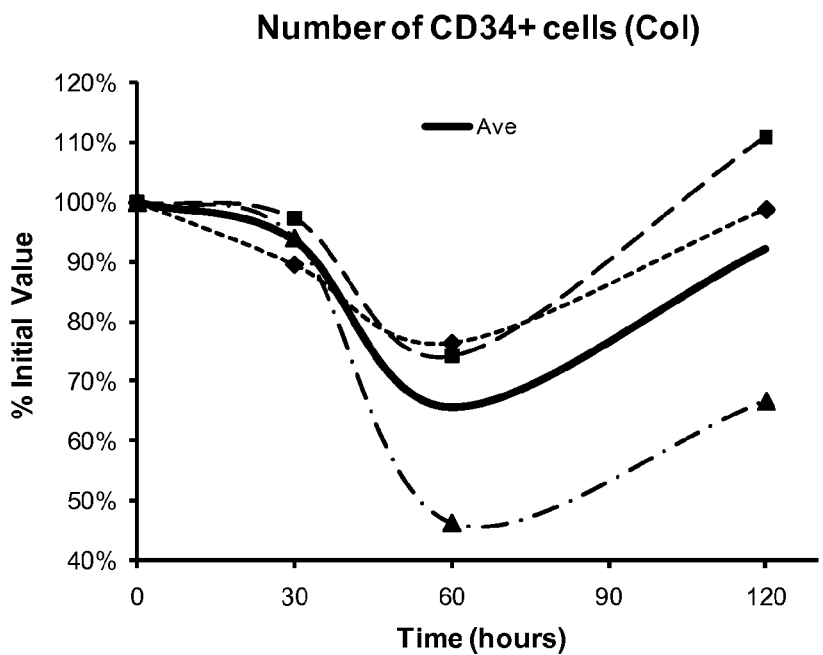

Figure 4.
A.
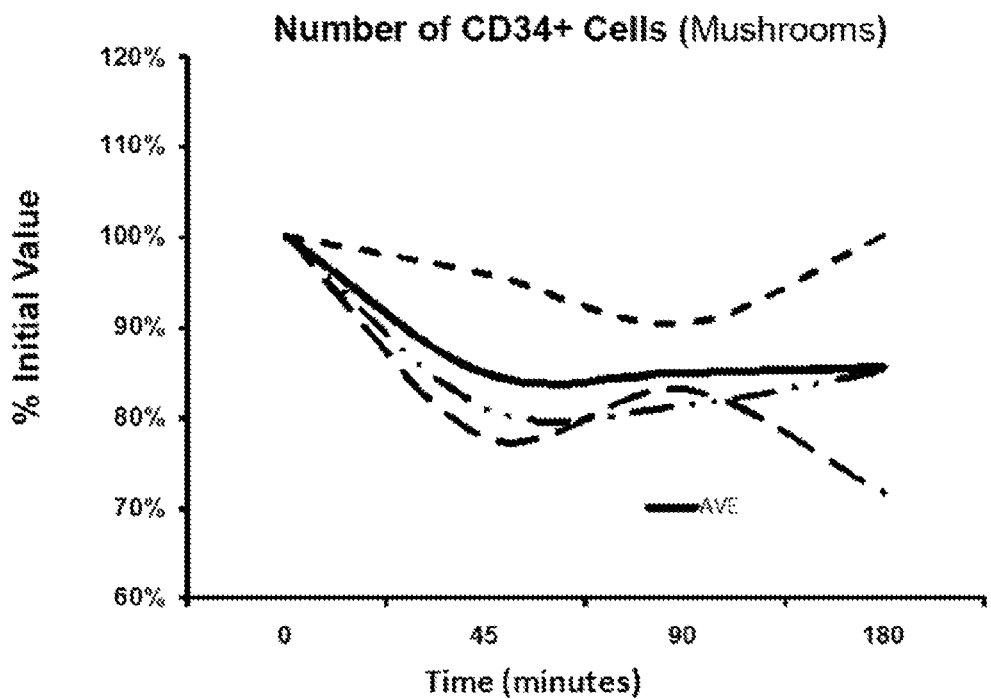
B.
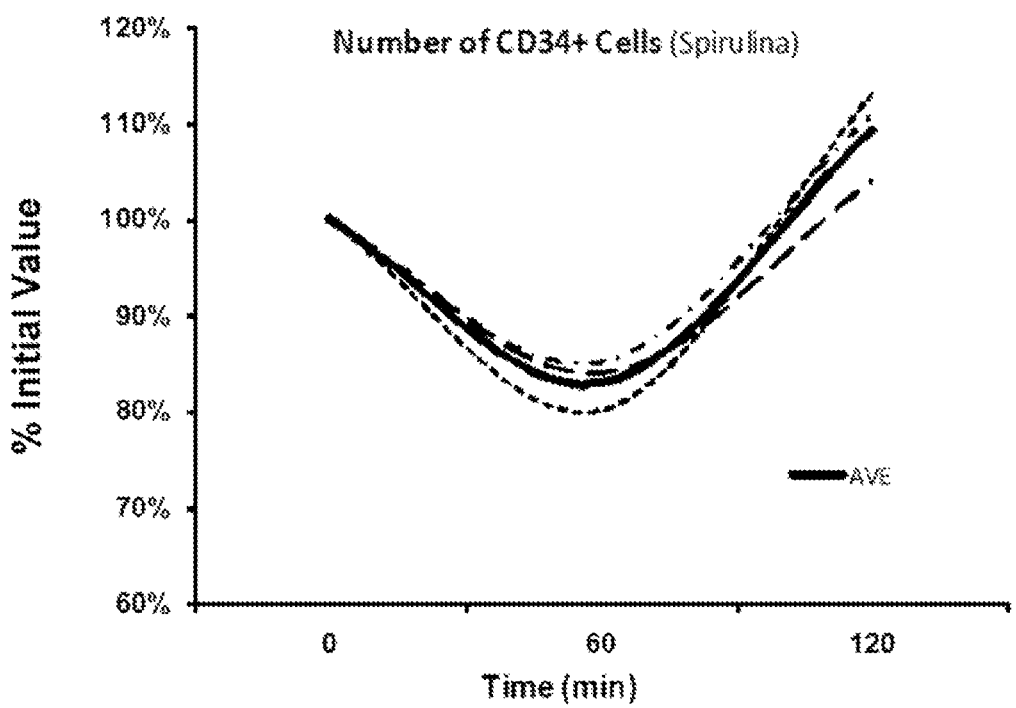

Figure 5.
A.
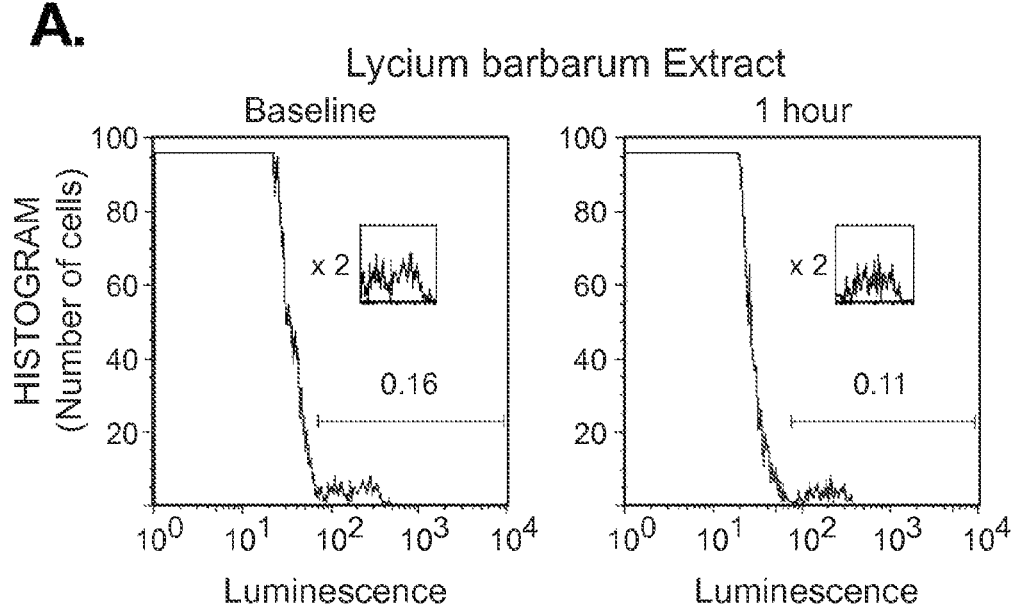
B.
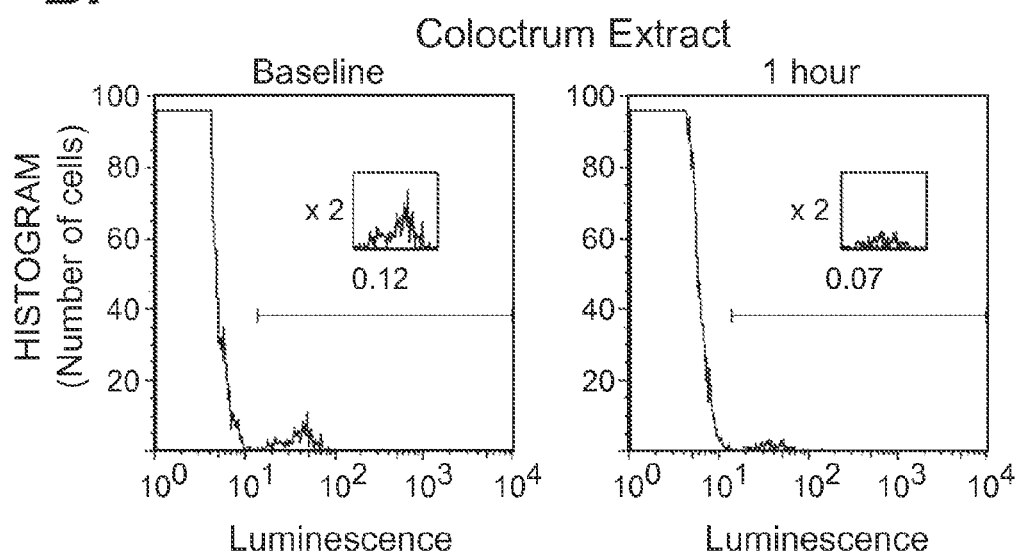

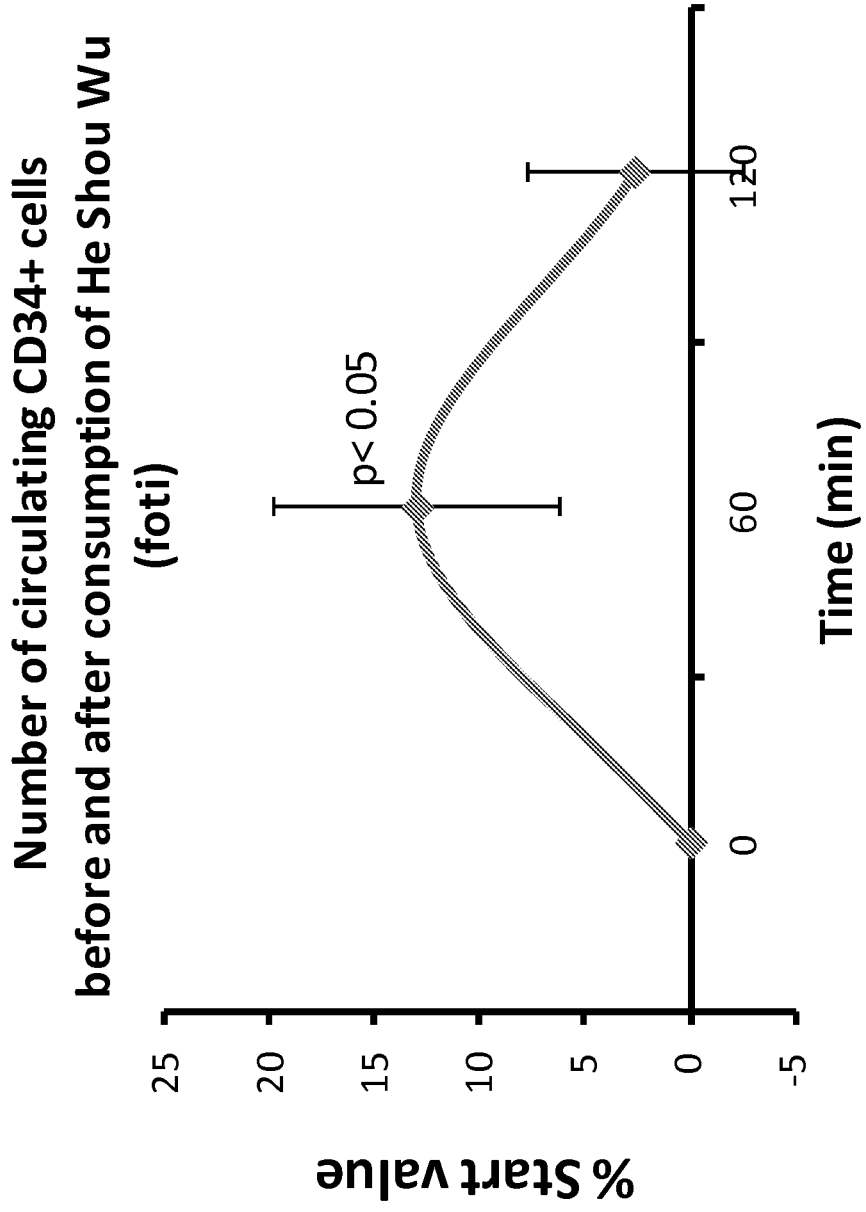
Figure 10. Number of circulating CD34+ cells before and after consumption of He Shou Wu (foti)

USE OF FOTI TO ENHANCE STEM CELL MOBILIZATION AND PROLIFERATION

CROSS-REFERENCE TO RELATED APPLICATIONS

This application is a National Phase of International Application No. PCT/US2012/065294, filed Nov. 15, 2012, which designated the U.S. and that International Application was published under PCT Article 21(2) in English. This application also includes a claim of priority under 35 U.S.C. 119(e) to U.S. provisional patent application No. 61/561,431, filed Nov. 18, 2011.

FIELD OF THE INVENTION

The present invention relates to methods and compositions for enhancing the mobilization of stem cells.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Stem cells (SCs) are defined as cells with the unique capacity to self-replicate throughout the entire life of an organism and to differentiate into various cell types of the body. Two well-known types of stem cells are embryonic stem cells and adult stem cells. Embryonic stem cells (ESCs) are extracted from 5-10 day old embryos called blastulas. Once isolated, ESCs can be grown in vitro and led to differentiate into various types of tissue cell (such as heart cells, liver cells, nervous cells, and kidney cells), after which they can be injected in specific tissues in order to regenerate the tissue.

Adult stem cells (ASCs) are undifferentiated or primitive cells that can self-renew and differentiate into specialized cells of various tissues and are found in any living organism after birth. ASCs have been isolated from various tissues such as the liver (oval cells) (Wang et al., 2003), the intestine (intestinal crypt stem cells) (Barker et al., 2008), muscles (satellite cells) (Kuang et al., 2008), the brain (neural stem cells) (Revishchin et al., 2008), and recently the pancreas (nestin positive pancreatic stem cells) (Burke et al., 2007). Umbilical cord stem cells and placental stem cells are considered ASCs.

The role of ASCs found in tissues (tissue stem cells) is to maintain and repair the tissue in which they are found, although recent studies have reported that ASCs from one tissue may have the ability to develop into cell types characteristic of other tissues. For example, oval cells in the liver were shown in vitro to have the ability to become insulin-producing pancreatic cells. (Yang et al. 2002) Nevertheless, the general view is that local stem cells are primarily involved in minor repair of the tissue in which they reside. In the case of significant injury or degeneration, the number of new tissue cells found in healing tissue far exceeds the capacity of local stem cells to duplicate and differentiate, suggesting that stem cells coming from other sites must be involved in the process of repair.

Although many tissues contain their own specific population of tissue stem cells, certain ASCs of key interest are those primarily found in the bone marrow and blood, Tissue stem cells are traditionally believed to be limited in their ability to differentiate into other tissues, however bone marrow stem cells (BMSC) were recently shown to have significant capability to become cells of other tissues.

It is difficult to freeze these processes in time to extract a cohesive, comprehensive portrait of regenerative mechanisms in the body. Nonetheless, enough information is available to affirm that different stem cells in the body, whether BMSCs, HSCs, marrow stromal cells (MSCs), multipotent adult progenitor cells (MAPCs), very small embryonic-like stem cells (VSEL), epiblast-like stem cell (ELSC) or blastomere-like stem cell (BLSC), constitute a broad component of the body's natural healing system. Since stem cells are capable of differentiating into a broad variety of cell types, they play an important role in the healing and regenerative processes of various tissues and organs. Bone marrow stem cells, including marrow stromal cells (MSCs), are released from tissues of origin, and circulate in a subject's circulatory or immune system to migrate into various organs and tissues to become mature, terminally differentiated cells. Therefore, enhancement of stem cell trafficking (i.e., release, circulation, homing and/or migration) can amplify these physiological processes and provide potential therapies for various pathologies. There are compositions and methods that utilize stem cell mobilization as a therapeutic approach. However, existing methods of promoting stem cell mobilization suffer from significant drawbacks, including poor kinetic performance, high cost, inconvenient methods of administration and unwanted side effects. One leading approach, injection of granulocyte colony-stimulating factor (G-CSF) or recombinant forms thereof, requires days to achieve peak circulating HSC numbers. The opposite problem exists with administration of interleukin-8 (IL-8), which acts only within minutes and has a short-lived effect on elevating circulating HSC levels in the bloodstream. (Frenette et al., 2000; Jensen et al., 2007) G-CSF and a different molecule, CXCR4 antagonist AMD3100, can have significant side effects, including hemorrhaging, rupturing of the spleen, bloody sputum, bone disorders, among others. Thus, there is a need in the art for an effective and convenient method for delivering stem cell mobilization agents to human subjects, to obtain positive clinical benefits without side effects and at a reduced cost.

Accordingly, the inventive compositions and methods disclosed herein enhance the release, circulation, homing and/or migration of stem cells within the body to promote healing and treatment of damaged tissues, as well as aid in the regeneration of tissues that suffer from some level of cellular loss, for greater vitality and reduced incidence of disease.

SUMMARY OF THE INVENTION

The present invention includes a method of increasing stem cell mobilization in a subject, including providing a mobilization agent capable of increasing stem cell mobilization, and administering a quantity of the mobilization agent to the subject in an amount sufficient to increase stem cell mobilization in the subject. In a different embodiment the mobilization agent is a composition including one or more of the following components selected from the group that includes: *Polygonum multiflorum* or extracts thereof, *Lycium barbarum* or extracts thereof, blue-green algae or extracts thereof, colostrum or extracts thereof, spirulina or extracts thereof, fucoidan, *Hericium erinaceus* or extracts thereof, *Ganoderma Lucidum* or extracts thereof, and *Cordyceps Sinensis* or extracts thereof. In a different embodiment, the mobilization agent is *Polygonum multiflorum* or extracts thereof. In a different embodiment, the stem cell is a bone marrow-derived stem cell (BMSC). In a different embodiment, the stem cell is a hematopoietic stem cell (HSC). In a different embodiment, administering the quantity comprises oral administration. In a different embodiment, the oral administration comprises use of a capsule or a pill.

Another aspect of the present invention described herein is a pharmaceutical composition including one or more of the following components selected from the group that is: *Polygonum multiflorum* or extracts thereof, *Lycium barbarum* or extracts thereof, blue-green algae or extracts thereof, colostrum or extracts thereof, spirulina or extracts thereof, fucoidan, *Hericium erinaceus* or extracts thereof, *Ganoderma Lucidum* or extracts thereof, and/or *Cordyceps Sinensis* or extracts thereof; and a pharmaceutically acceptable carrier. In a different embodiment, the quantity of *Polygonum multiflorum* or extracts thereof, comprises 10-2000 mg in a single dose. In a different embodiment, the quantity of *Lycium barbarum* or extracts thereof, comprises 10-2000 mg in a single dose. In a different embodiment, the quantity of blue-green algae or extracts thereof, comprises 10-2000 mg in a single dose. In a different embodiment, the quantity of colostrum or extracts thereof, comprises 10-300 mg in a single dose. In a different embodiment, the quantity of spirulina or extracts thereof, comprises 10-300 mg in a single dose. In a different embodiment, the quantity of fucoidan or extracts thereof, comprises 10-2000 mg in a single dose. In a different embodiment, the quantity of *Hericium erinaceus* or extracts thereof, *Ganoderma Lucidum* or extracts thereof, and/or *Cordyceps Sinensis* or extracts thereof comprises 10-1000 mg in a single dose.

Another aspect of the present invention described herein is method of preparing an extract of *Polygonum multiflorum* including providing a quantity of *Polygonum multiflorum*, crushing the *Polygonum multiflorum* into a solid powder, drying the solid powder, immersing the solid powder in a solvent, and separating the solid power from the solvent, wherein the solvent includes an extract of *Polygonum multiflorum*. In a different embodiment, immersing the solid powder is in a solvent that is water or another aqueous solution at a low temperature. In a different embodiment, the low temperature is approximately 4° C. In a different embodiment, immersing the solid powder is in a solvent that is an organic solvent at a high temperature. In a different embodiment, the high temperature is near the boiling point of the organic solvent. In a different embodiment, the organic solvent is methanol or ethanol. In a different embodiment, the *Polygonum multiflorum* is frozen before crushing.

BRIEF DESCRIPTION OF THE FIGURES

Exemplary embodiments are illustrated in referenced figures. It is intended that the embodiments and figures disclosed herein are to be considered illustrative rather than restrictive.

FIG. 3 provides graphs illustrating a typical time course of stem cell migration in the human body after consumption of (A) whole *Lycium barbarum* (LB) fruit and (B) colostrum (Col), in accordance with various embodiments of the present invention. For both products, the thin lines show individual responses. For LB, the thick dotted line is the average response while the thick line shows the time course of the response with the average peak response at 45 minutes. For Col, all participants peaked at 60 minutes, so the thick lines show the average time course of the response.

FIG. 4 provides a graph illustrating a typical time course of stem cell migration in the human body after consumption of (A) a polysaccharide rich fraction of mushroom (*Cordyceps sinensis, Ganoderma lucidum, Hericium erinaceus*), and (B) spirulina or an extract thereof, in accordance with an embodiment of the present invention.

FIG. 10 depicts the results of consuming a combination of *Polygonum multiflorum*, blue-green algae, and fucoidan in accordance with various embodiments of the present invention. Consumption of the combination including *Polygonum multiflorum* resulted in a transitory increase in the number of circulating stem cells compared to placebo under the same conditions. The combination containing *Polygonum multiflorum* was shown to trigger a modest increase in the number of circulating stem cells by 13±6% (n=7) (p<0.05). The increase exceeded 25% in 2 of the participants.

DETAILED DESCRIPTION OF THE INVENTION

Figure 1:
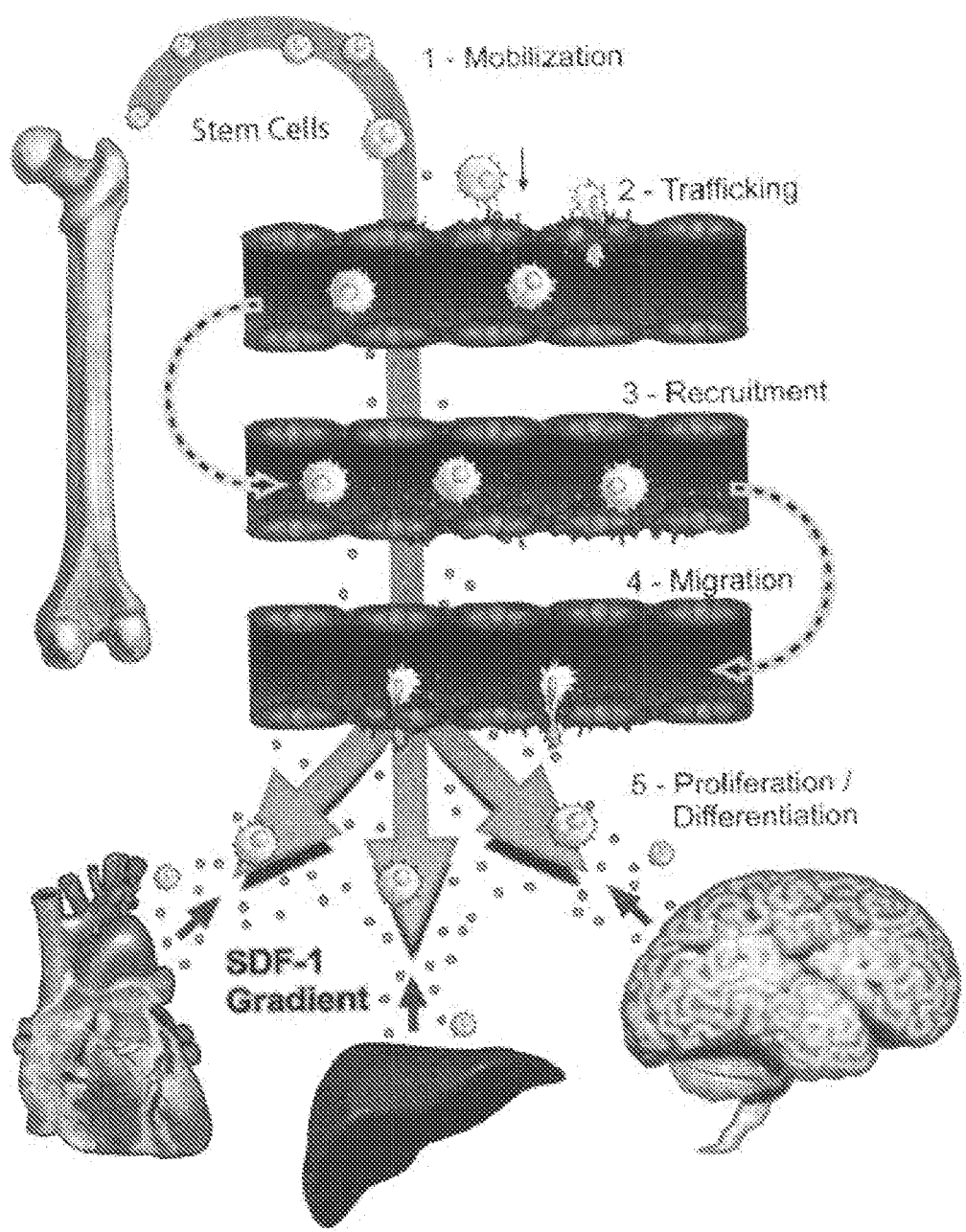
FIG. 1 depicts mobilization and migration of endogenous stem cells in accordance with various embodiments of the present invention. Under normal physiological conditions or in response to disease or injury, hematopoietic stem cells mobilize from compartments such as bone (A) and circulate into the bloodstream (B), migrate towards tissues to promote repair and regeneration in different parts of the body (C).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russell, *Molecular Cloning: A Laboratory Manual* 3rd ed., Cold Spring Harbor Laboratory Press (Cold Spring Harbor, N.Y. 2001), *Remington's Pharmaceutical Sciences*, by E. W. Martin, Mack Publishing Co., Easton, Pa., 15th Edition (1975), describes compositions and formulations suitable for pharmaceutical delivery of the inventive compositions described herein provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods described herein. For purposes of the present invention, the following terms are defined below.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Blue-green algae" as used herein refers to the common name for gram-negative photosynthetic bacteria belonging to division *Cyanophyta* that may exist in unicellular, colonial, or filamentous forms. Representative blue-green algae include, but are not limited to, *Spirulina* and *Aphanizomenon* species, one example being the *Aphanizomenon flos aquae* (AFA) species of blue-green algae. "Algae" is the plural form of "alga," which is a cell of a microalgae species. For example, "blue green algae" refers to multiple cells of a single *Aphanizomenon* species, multiple cells of a single *Spirulina* species, or a mixture of cells from multiple *Aphanizomenon* and/or *Spirulina* species.

"Circulatory system" as used herein refers to the mechanisms for moving blood and blood components throughout the body of a subject, including the vascular and lymph systems. The mechanisms of the circulatory system include, but are not limited to, the heart, blood vessels (arteries, veins, and capillaries), and lymph vessels.

"Colostrum" as used herein refers to a fluid secreted by the mammary glands of female mammals during the first few days of lactation, containing various nutrients and protease inhibitors that keep it from being destroyed by the processes of digestion. Humans produce relatively small amounts of colostrum in the first two days after giving birth, but cows produce about nine gallons of colostrum. Colostrum contains concentrated levels of important immune modulators, including Transfer Factor, PRP, IGF-1, n-acetyl neuraminic acid, GMP, nucleic acid and defensins. Colostrum extracts have been shown to activate phagocytosis by monocytes and increase the reactive oxygen burst in polymorph nucleated cells. Colostrum was also shown to trigger natural killer (NK) cell activation and also trigger the secretion of anti-inflammatory cytokines in in vitro cell-based assays. References herein to colostrum also include derivatives and artificial substitutes thereof.

"Component of *Polygonum multiflorum*" as used herein refers to any fraction, extract, or isolated or purified molecule from *Polygonum multiflorum*. For example, the component is a protein or nucleic acid or a polysaccharide, a phytochemical, or a fraction of *Polygonum multiflorum*. Thus, in certain embodiments of the invention, components of *Polygonum multiflorum* are obtained by disrupting *Polygonum multiflorum*, adding an inorganic or organic solvent, and collecting fractions. Specific, non-limiting examples of fractions are isolated using high performance liquid chromatography, thin layer chromatography, or distillation. Fractionation may be based on the molecular weight or the hydrophobicity of the components of *Polygonum multiflorum*. Examples of components found in *Polygonum multiflorum* include hydroxyl stilbenes, anthraquinones and derivatives, lecithin, chrysophanic acid, emodin, rhein, chrysophanic acid anthrone, and 2,3,5, 4'-tetrahydroxystilbene-2-O-βD-glucoside, among others.

"Component of *Lycium barbarum*" as used herein refers to any fraction, extract, or isolated or purified molecule from *Lycium barbarum*. For example, the component is a protein or nucleic acid or a polysaccharide, a phytochemical, or a fraction of *Lycium barbarum*. Thus, in certain embodiments of the invention, components of *Lycium barbarum* are obtained by disrupting *Lycium barbarum*, adding an inorganic or organic solvent, and collecting fractions. Specific, non-limiting examples of fractions are isolated using high performance liquid chromatography, thin layer chromatography, or distillation. Fractionation may be based on the molecular weight or the hydrophobicity of the components of *Lycium barbarum*.

"Differentiation" as used herein refers to the process by which cells become more specialized to perform biological functions. For example, hematopoietic stem cells, hematopoietic progenitors and/or stem cells may change from multipotent stem cells into cells committed to a specific lineage and/or cells having characteristic functions, such as mature somatic cells. Differentiation is a property that is often totally or partially lost by cells that have undergone malignant transformation.

"Enhancement," "enhance" or "enhancing" as used herein refers to an improvement in the performance of or other physiologically beneficial increase in a particular parameter of a cell or organism. At times, enhancement of a phenomenon is quantified as a decrease in the measurements of a specific parameter. For example, migration of stem cells may be measured as a reduction in the number of stem cells circulating in the circulatory system, but this nonetheless may represent an enhancement in the migration of these cells to areas of the body where they may perform or facilitate a beneficial physiologic result, including, but not limited to, differentiating into cells that replace or correct lost or damaged function. In one embodiment, enhancement refers to a 15%, 20%, 30% or greater than 50% reduction in the number of circulating stem cells. In one specific, non-limiting example, enhancement of stem cell migration may result in or be measured by a decrease in a population of the cells of a non-hematopoietic lineage, such as a 15%, 20%, 30%, 50%, 75% or greater decrease in the population of cells or the response of the population of cells. In one embodiment, an enhanced parameter is the trafficking of stem cells. In one embodiment, the enhanced parameter is the release of stem cells from a tissue of origin. In one embodiment, an enhanced parameter is the migration of stem cells. In another embodiment, the parameter is the differentiation of stem cells. In yet another embodiment, the parameter is the homing of stem cells.

"Fucoidan" as used herein describes sulfated fucans obtained from algae. Fucoidan has been obtained from a broad range Algae species as provided in the following non-exhaustive list: *Cladosiphon okamuranus, Chordaria flagelliformis*, Ch. *Gracilis, Saundersella simplex, Desmaestia intermedia, Dictyosiphon foeniculaceus, Dictyota dichotoma, Padina pavonica, Spatoglussum, schroederi, Adernocystis utricularis, Pylayella littoralis, Ascophyllum nodosum, Bifurcaria bifurcata, Fucus. Visculosus, F. spiralis, F. serratus, F. evaescens, Himanthalia lorea, Hizikia fusiforme, Pelvetia canaliculata, P. wrightii, Sargassum stenophyllum, S. honeri, S. Khellmanium, S. muticum, Alaria fistulosa, A. marginata, Arthrothammus bifidus, Chorda film, Ecklonia kurome, E. cava, Eisenia bicyclis, Laminaria angustata, L. brasiliensis, L. cloustoni, L. digitata, L. japonica, L. religiosia, L. saccharina, Macrocystis integrifolia, M. pyrifera, Nereocystis luetkeana, Undaria pinnatifida, Petalonia fascia, Scytosiphon lomentaria*. Substantial pharmaceutical research has been done on fucoidan, focusing primarily on two distinct forms: F-fucoidan, which is >95% composed of sulfated esters of fucose, and U-fucoidan, which is approximately 20% glucuronic acid, each of which is included in the term "fucoidan" as used herein. Depending on the source of the fucoidan, fucoidan can serve as a releasing agent in certain embodiments, while in other embodiments, fucoidan can serve as a migration agent.

"Hematopoiesis" as used herein refers to the formation and development of blood cells. Prenatally, hematopoiesis occurs in the yolk sack, then liver, and eventually the bone marrow. In normal adults, it occurs primarily in bone marrow and lymphatic tissues. All blood cells develop from pluripotent stem cells, which are committed to three, two, or one hematopoietic differentiation pathways. This includes the production of hematopoietic cells including B-cells, T-cells, cells of the monocyte macrophage lineage, and red blood cells.

"Hematopoietic agent" as used herein refers to a compound, antibody, nucleic acid molecule, protein, cell or other molecule that affects hematopoiesis. A molecular agent can be a naturally-occurring molecule or a synthetic molecule. In some instances, the agent affects the growth, proliferation, maturation, migration or differentiation or release of hematopoietic cells. In various embodiments, the agent is *Polygonum multiflorum* or an extract or component of *Polygonum multiflorum*.

"Hematopoietic stem cells" as used in the present invention means multipotent stem cells that are capable of eventually differentiating into all blood cells including, erythrocytes, leukocytes, megakaryocytes, and platelets. This may involve an intermediate stage of differentiation into progenitor cells or blast cells. The term "hematopoietic progenitors", "progenitor cells" or "blast cells" are used interchangeably in the present invention and describe maturing HSCs with reduced differentiation potential, but are still capable of maturing into different cells of a specific lineage, such as myeloid or lymphoid lineage. "Hematopoietic progenitors" include erythroid burst forming units, granulocyte, erythroid, macrophage, megakaryocyte colony forming units, granulocyte, erythroid, macrophage, and granulocyte macrophage colony-forming units.

"Homing" as used herein refers to the process of a cell migrating from the circulatory system into a tissue or organ. In some instances, homing is accomplished via tissue-specific adhesion molecules and adhesion processes. Homing may refer to the migration back to the bone marrow.

"Immunologically normal" as used herein refers to a subject that displays immune system characteristics typical for the species to which the individual belongs. These typical characteristics include, among others, functioning B-cells and T-cells as well as structural cell components, called cell surface antigens, which act as the immunologic signature for a particular organism.

"Immunologically compromised" as used herein refers to a subject having a genotypic or a phenotypic immunodeficiency. A genotypically-immunodeficient subject has a genetic defect that results in an inability to generate either humoral or cell-mediated responses. A specific, non-limiting example of a genotypically immunodeficient subject is a genotypically immunodeficient mouse, such as a SCID mouse or a bg/nu/xid mouse. A "phenotypically-immunodeficient subject" is a subject, which is genetically capable of generating an immune response, which has been phenotypically altered such that no response is seen. In one specific, non-limiting example, a phenotypically-immunodeficient recipient has been irradiated. In another specific, non-limiting example, a phenotypically-immunodeficient subject has been treated with chemotherapy. In yet another specific, non-limiting example, the phenotypically-immunodeficient subject has suffered a bacterial or viral infection, such as the human immunodeficiency virus (HIV) or simian immunodeficiency virus (SIV).

"Isolated biological component" (such as a nucleic acid molecule, polypeptide, polysaccharide or other biological molecule) as used herein refers to a biological component that has been substantially separated or purified away from other biological components in which the component naturally occurs. Nucleic acids and proteins may be isolated by standard purification methods, recombinant expression in a host cell, or chemically synthesized.

"*Lycium barbarum*" or "*L. barbarum*" as used herein refers to a small bright orange-red, ellipsoid berry or fruit grown. One exemplary source is in the north of China, primarily in the Ningxia Hui Autonomous Region. It is sometimes referred to as goji berry or wolfberry. *L. barbarum* belongs to the Solanaceae family, the nightshade family that includes hundreds of plant foods like potato, tomato, eggplant, and peppers (paprika).

"Lymphoproliferation" as used herein refers to an increase in the production of lymphocytes.

"Modulation" or "modulates" or "modulating" as used herein refers to upregulation (i.e., activation or stimulation), down regulation (i.e., inhibition or suppression) of a response or the two in combination or apart.

"Migration" as used herein refers to the central process for movement of cells in the development and maintenance of multicellular organisms. Cells often migrate in response to, and towards, specific external signals, commonly referred to as chemotaxis. Migration includes the process of a cell moving from the circulatory system into a tissue or organ. More specifically, circulating stem cells are tethered to the surface of capillary endothelium via expression of adhesion molecules of cell surfaces, resulting in cytoskeletal changes in both endothelium and stem cells, and allowing movement through the capillary wall en route to a tissue and/or organ site. In some instances, homing is accomplished via tissue-specific adhesion molecules and adhesion processes.

"Migration agent" as used herein are mobilization agents capable of promoting the process of a cell moving from the circulatory system into a tissue or organ. Migration of stem cells may be demonstrated, for example, by a decrease in circulating stem cells in the circulatory or immune system, or by the expression of surface markers and/or adhesion molecules on cell surfaces, which relate to homing, tethering, and/or extravasation of circulating stem cells to the surface of vessels such as capillary endothelium. Examples of migration agents include isolated or purified components extracted from *Polygonum multiflorum* or extracts thereof, *Lycium barbarum*, including a polysaccharide-rich fraction (fraction A) of *Lycium barbarum* extract, colostrum, including a protein-rich fraction (fraction B) of colostrum extract, fucoidan, including an isolated component or compound extracted from an algae, such as a compound found in a polysaccharide-rich fraction (fraction C) of algae extracts, including *Chordaria cladosiphon*, or other algaes, or extracts thereof, mushrooms, including an isolated component or compound extracted from a mushroom, such as a compound found in a polysaccharide-rich fraction (fraction D) of mushroom extracts, including *Cordyceps sinensis* or an extract thereof, *Ganoderma lucidum* or an extract thereof, *Hericium erinaceus* or an extract thereof, spirulina, including *Arthrospira platensis*, *Arthrospira maxima*, or extracts thereof. In different embodiments, this agent affects the migration of stem cells, such as $CD34^{high}$ (CD34+) cells. In one embodiment, the migration agent decreases the number of bone marrow-derived stem cells and/or hematopoietic stem cells circulating in the peripheral blood. In another embodiment, the migration agent relates to enhanced expression of CXCR4 on circulating stem cells.

"Mushroom polysaccharides" as used herein refers to glucans found mainly in various species of mushrooms such as *Cordyceps sinesis*, *Hercicium erinaceous*, and *Ganoderma lucidum*. This also includes the numerous bioactive polysaccharides or polysaccharide-protein complexes from medicinal mushrooms that may enhance innate and cell-mediated immune responses, and exhibit antitumor activities in animals and humans.

"Pharmaceutically acceptable carriers" as used herein refer to conventional pharmaceutically acceptable carriers useful in this invention.

"*Polygonum multiflorum*" or "*P. multiflorum*", as used herein, refers to a species of herbaceous perennial vine growing to 2-4 m tall from a woody tuber native to central and southern China. Leaves are 3-7 cm long and 2-5 cm broad, broad arrowhead-shaped, with an entire margin. Flowers are 6-7 mm diameter, white or greenish-white, produced on short, dense panicles up to 10-20 cm long. Fruit is an achene 2.5-3 mm long. It is also known as *Fallopia multiflora, Radix Polygoni, Radix Polygoni* Multiflori, fleeceflower, He Shou Wu, or Fo-Ti.

"Polysaccharide" as used herein refers to a polymer of more than about ten monosaccharide residues linked glycosidically in branched or unbranched chains.

"Progenitor cell" as used herein refers to a cell that gives rise to progeny in a defined cell lineage.

"Promote" and/or "promoting" as used herein refer to an augmentation in a particular behavior of a cell or organism. In one embodiment, promoting relates to the mobilization of melanocyte derived stem cells. In another embodiment, promoting relates to the differentiation of stem cells into melanocytes.

"Recruitment" of a stem cell as used herein refers to a process whereby a stem cell in the circulatory system migrates into specific site within a tissue or organ. Recruitment may be facilitated by a compound or molecule, such as a chemoattractant signal or cell receptor. For example, both CXCR4 and SDF-1 have identified roles in stem cell homing and migration.

"Releasing agent" as used herein are mobilization agents capable of promoting the release and egress of stem cells from a tissue of origin. Release of stem cells from a tissue of origin may be demonstrated, for example, by an increase in circulating stem cells in the circulatory or immune system, or by the expression of markers related to egress of stem cells from a tissue of origin, such as bone marrow. Examples of releasing agents include fucoidan, as obtained from an extract of algae such as *Undaria pinnatifida*, and *Polygonum multiflorum* or extracts thereof. In one embodiment, the releasing agent increases the number of bone marrow-derived stem cells and/or hematopoietic stem cells in the peripheral blood. In another embodiment, the releasing agent affects the number of stem cells, such as $CD34^{high}$ (CD34+) cells, circulating in the peripheral blood.

"Satellite cell" as used herein refers to a muscle-specific stem cell, often located in the periphery of muscle tissue, and capable of migrating into a muscle to aid in tissue repair and reconstruction.

"Stem cells" as used herein are cells that are not terminally differentiated and are therefore able to produce cells of other types. Characteristic of stem cells is the potential to develop into mature cells that have particular shapes and specialized functions, such as heart cells, skin cells, or nerve cells. Stem cells are divided into three types, including totipotent, pluripotent, and multipotent. "Totipotent stem cells" can grow and differentiate into any cell in the body and thus, can form the cells and tissues of an entire organism. "Pluripotent stem cells" are capable of self-renewal and differentiation into more than one cell or tissue type. "Multipotent stem cells" are clonal cells that are capable of self-renewal, as well as differentiation into adult cell or tissue types. Multipotent stem cell differentiation may involve an intermediate stage of differentiation into progenitor cells or blast cells of reduced differentiation potential, but are still capable of maturing into different cells of a specific lineage. The term "stem cells", as used herein, refers to pluripotent stem cells and multipotent stem cells capable of self-renewal and differentiation. "Bone marrow-derived stem cells" are the most primitive stem cells found in the bone marrow which can reconstitute the hematopoietic system, possess endothelial, mesenchymal, and pluripotent capabilities. Stem cells may reside in the bone marrow, either as an adherent stromal cell type, or as a more differentiated cell that expresses CD34, either on the cell surface or in a manner where the cell is negative for cell surface CD34. "Adult stem cells" are a population of stem cells found in adult organisms with some potential for self-renewal and are capable of differentiation into multiple cell types. Other examples of stem cells are marrow stromal cells (MSCs), HSC, multipotent adult progenitor cells (MAPCs), very small embryonic-like stem cells (VSEL), epiblast-like stem cell (ELSC) or blastomere-like stem cell (BLSC).

"Stem cell circulation agent" (SCCA), "mobilization agent", and/or "mobilization factor" as used herein refers to one or more compounds, antibodies, nucleic acid molecules, proteins, polysaccharides, cells, or other molecules, including, but not limited to, neuropeptides and other signaling molecules, that affects the release, circulation, homing and/or migration of stem cells from the circulatory system into tissue or organ. A molecular agent may be a naturally occurring molecule or a synthetic molecule. Examples of mobilization agents include "releasing agents", wherein a releasing agent is capable of promoting the egress of stem cells from a tissue of origin and also "migration agents", wherein a migration agent is capable of promoting the process of a cell moving from the circulatory system into a tissue or organ.

"Subject" as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. For example, this can be the amount effective for enhancing migration of stem cells that replenish, repair, or rejuvenate tissue. In another embodiment, a "therapeutically effective amount" is an amount effective for enhancing trafficking of stem cells, such as increasing release of stem cells, as can be demonstrated by elevated levels of circulating stem cells in the bloodstream. In still another embodiment, the "therapeutically effective amount" is an amount effective for enhancing homing and migration of stem cells from the circulatory system to various tissues or organs, as can be demonstrated be decreased level of circulating stem cells in the bloodstream and/or expression of surface markers related to homing and migration. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Trafficking" as used herein refers to the process of movement of a cell from the tissue of origin, traveling within the circulatory or immune system, and localization towards a site within a tissue and/or organ. Trafficking also includes stem cell mobilization, beginning with release from a tissue of origin, such as egress of stem cells from bone marrow. Trafficking further includes movement of a cell from the tissue of origin, homing by adhesion to the endothelium, transmigration, and final migration within the target tissue and/or organ. Furthermore, trafficking may include the process of movement of a cell of the immune system. One specific, non-limiting example of trafficking is the movement of a stem cell to a target organ, also referred to as migration. Another specific, non-limiting example of trafficking is the movement of a B-cell or a pre-B-cell leaving the bone marrow and moving to a target organ.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

As described, stem cells are unique cells that possess the capacity to differentiate into more specialized cells. One particular type of stem cell, hematopoietic stem cells (HSCs), are capable of differentiating into many different types of blood cells. In addition, HSCs typically reside in the bone marrow, where proliferation and self-renewal of the cells allows HSCs to be involved in the support and maintenance of the hematopoietic system. Existing scientific literature has chiefly focused on HSCs' potential to develop into hematopoietic lineage cells derivatives. Emerging evidence has further identified the capacity for HSCs to also differentiate into non-hematopoietic, tissue specific cells. Recently, HSCs have been found to possess the capacity to differentiate into a variety of tissue-specific cell types, such as myocytes, hepatocytes, osteocytes, glial cells, and neurons. As a result, HSCs form blood and immune cells that are responsible for constant maintenance and immune protection of virtually every cell type of the body.

Similarly, bone marrow stem cells (BMSCs) were recently shown to have significant capability to become cells of other tissues. In the bone marrow, stem cells duplicate using a process known as "asymmetrical cellular division" according to which the two daughter cells are not identical; one cell retains the original DNA and remains in the bone marrow whereas the other cell contains the DNA copies and is released in the blood where it migrates into various tissues in need of repair. BMSCs have been traditionally considered to have little potential for plasticity, being limited in their development to red blood cells, lymphocytes, platelets, bone and connective tissue. However, much scientific work has been published over the past few years that demonstrates the exceptional plasticity of BMSC. For example, after transplantation, BMSCs and HSCs were shown to have the ability to become muscle cells (Abedi et al., 2004), heart cells (Fraser et al., 2004), endothelium capillary cells (Asahara et al., 1999), liver cells (Jang et al., 2004), as well as lung, (Krause et al., 2001), gut (Krause et al., 2001), skin (Branski et al., 2008), and brain cells (Dezawa et al., 2005). As a further illustrative example, Jang et al. (2004) performed an experiment which not only demonstrated the ability of HSC to become liver cells upon contact with specific liver-derived molecules, but this process took place within hours. Briefly, HSCs were co-cultured with either normal or damaged liver tissue separated by a semi-permeable membrane (pores large enough to let molecules pass through, but small enough to prevent the passage of cells from one compartment to the other, pore size 0.4 $\mu$m). Using immunofluorescence assay methods to detect molecules specific for either HSCs (CD45) or liver cells (albumin), the researchers could follow the transformation of the population of cells placed in the upper compartment. When HSCs were cultured alone for 8 hours, they only expressed CD45 and no albumin, indicating that no HSCs had differentiated into liver cells. However, when HSCs were exposed to injured liver tissue, they rapidly became positive for albumin. Over time, the population of cells positive for CD45 began to decrease as the population positive for albumin began to increase. Albumin-positive cells were seen as early as 8 hours into the procedure and increased in frequency to 3.0% at 48 hours. The conversion was minimal and delayed when HSCs were exposed to undamaged liver (control for injury).

Because HSCs and BMSCs play an important role in the healing and regenerative processes of various tissues and organs in the body beyond their traditional role in maintaining hematopoietic and immune systems of the body, activation and enhancement of stem cell trafficking may amplify these physiological processes and provide a potential therapy for various pathologies. The classic source of HSCs and BMSCs is bone marrow, which includes hip, ribs, sternum and other bone structures. Bone provides a unique regulatory microenvironment for HSCs and BMSCs, including interaction with a specific mesenchymal cell type (the osteoblast), extracellular matrix glycoproteins and a uniquely rich mineral signature. (Adams and Scadden, 2006) This stem cell "niche" contains a great deal of critical molecular interactions which guide the response of stem cells to specific physiological conditions. The niche may be an important focal point for changes in the state of tissue that result in a change in the regenerative processes rooted in stem cell activity. (Adams and Scadden, 2006)

Beyond populations of HSCs found in bone marrow, HSCs are also present in the peripheral bloodstream of normal, healthy persons. It has been known for decades that a small number of stem and progenitor cells circulate in the bloodstream, but more recent studies have shown that greater numbers of HSCs can be coaxed into mobilization from marrow to blood by injecting the donor with a cytokine, such as granulocyte-colony stimulating factor (G-CSF). Despite this advance, the natural process by which stem cells are released from bone marrow and migrate towards a site within tissue and/or an organ is not fully understood. A leading model involves the chemokine, Stromal-Derived Factor-1 (SDF-1) and its specific receptor, CXCR4. In this capacity, the binding of SDF-1 to CXCR4, leads to adherence of stem cells to bone marrow through increased expression of adhesion molecules on the cell membrane surface. Disruption of adhesion of stem cells to bone marrow thus promotes mobilization of stem cells into the peripheral bloodstream. (FIG. 1C) Some factors such as G-CSF or IL-8 may interfere with adhesion through elevated activation of protelytic enzymes or degradation of the SDF-1 ligand. (Drapeau 2010) Other types of molecules, such as L-selectin blockers, may instead down-regulate CXCR4 expression which in turn reduces stem cell adhesion to the bone marrow environment. Generally speaking enhancing binding of SDF-1 to CXCR4 promote adherence, therefore L-selectin blockers such as sulfated fucans, which reduces CXCR4 expression, can trigger stem cell mobilization. (Drapeau 2010)

Stem cells circulating in the peripheral bloodstream are recruited to sites of tissue in need of repair and regeneration through homing and extravasation. This mobilization of stem cells into the bloodstream and subsequent migration to the site of tissue injury results from a combination of mechanical and chemoattractant signals. (Drapeau 2010) Mechanical force or other factors may activate L-selectins on the surface of stem cells. Activation of L-selectins, in turn, may promote elevated expression of the receptor, CXCR4. Cells at the site of tissue injury may also secrete SDF-1 ligand, thereby attracting stem cells expressing receptor CXCR4 to the injury site. The interaction of SDF-1 and CXCR4 promotes sufficient adhesion to halt circulation of a stem cell in the peripheral blood stream. (FIG. 1B) Based on this model, L-selectin blockers such as sulfated fucans, may possess a critical capacity to mobilize HSCs into the bloodstream, with subsequent homing, extravasation and migration into tissue promoting regenerative maintenance and repair of cells and tissues in an organism. Whereas G-CSF is released from injured tissue and its presence in the bloodstream triggers HSC release from bone marrow, dietary supplements composed of L-selectin blockers may possibly support the phenomenon of natural regeneration and repair in the body.

Remarkably, in ancient traditional Chinese medicine (TCM) literature, there is description of similar processes, including a concept called the Jing. Although the term has changed over time and today refers to essentially to "semen", ancient texts referred to two different Jing: one primordial that was present at the time of conception and led to the formation of the fetus, and the other that remained in the body and was regenerative and healing. Modernly, the notion of an innate healing and regenerative capacity, as exemplified by the TCM concept of Jing, is consistent with the remarkable capacity of embryonic and adult stem cells to facilitate these processes. (Yang et al. 2009) It is interesting to note that herbs known to support the Jing are used to "tonify the blood", turn back hair to their natural color, and for overall regenerative properties. An example is goji berry (*Lycium barbarum*), which is known to support the Jing and is used for longevity; goji berry has been shown to support stem cell migration.

Another example is StemEnhance, a supplement containing blue-algae *Aphanizomenon flos aquae* (AFA), that is known to support stem cell mobilization, has been was shown to help reverse hair color and support overall healing and regeneration. (Jensen et al., 2007) As compositions such as StemEnhance influence stem cell activity in the body, these effects may be understood as stimulating the Jing. Conversely, it is of great interest to understand if TCM medicines and herbs known to stimulate the Jing can be demonstrated as possessing effects on stem cell activities such as proliferation, migration and mobilization. The inventors therefore studied the effects of a widely used herb to stimulate the Jing, *Polygonum multiflorum*, with a particular view towards effects on stem cell migration and mobilization.

Polygonum multiflorum.

The dried root tuber of *Polygonum multiflorum* plant, also known as fleeceflower root, has been used as a traditional Chinese medicine called He shou wu, this medication gaining notoriety in TCM from a tale of a famous Chinese military officer condemned to death and jailed without food or drink. Surviving by consuming the leaves and roots of the vinelike weed, *Polygonum multiflorum*, the officer's captors later found his remains as still having lustrous black hair. While the origins of this tale are apocryphal, they serve to illustrate the long-held notion that *Polygonum multiflorum* possesses important properties for tapping into the regenerative and restorative potential of the body. Recent scientific studies have confirmed that extracts of *Polygonum multiflorum* are indeed capable of promoting hair follicle growth, through increased expression of sonic hedgehog (Shh) and β-catenin expression—two important pathways involved in both early embryogenesis and maintaining stem cell identity. (Park et al. 2011)

Further analysis of *Polygonum multiflorum* extracts have confirmed this plant to be a rich source of bioactive compounds, two notable examples being anthraquinones and derivatives and hydroxy stilbenes. Anthraquinones and derivatives have served as the basis for antimalarial, laxative, and chemotherapy treatments. Hydroxyl stilbenes, such as 2,3,5,4'-tetrahydroxystilbene-2-O-β-D-glucoside, have been show to provide important neuroprotective effects warding off symptoms of different neurodegenerative diseases. Together, these results indicate that components of *Polygonum multiflorum* extracts possess important properties for healing and regenerating the body, possibly by modulating inflammation, reducing risk of cancer proliferation, and/or providing protective effects for cells, tissues, and organs of the body.

While effects of these components in *Polygonum multiflorum* is somewhat understood for certain specific conditions, there is much less knowledge about how components of *Polygonum multiflorum* may specifically influence stem cell activity in the body. This is surprising given that, as described, stem cells play an integral role in the body's natural healing and regeneration mechanisms. One of the few existing studies on the subject indicates that *Polygonum multiflorum* extracts promotes proliferation of stem cells and progenitors, as shown by an increase in the number of bone marrow stem cells and lymphoid progenitors following administration of *Polygonum multiflorum* extracts in mice. (Zhiweng et al. 1991). Similarly, U.S. patent application Ser. No. 12/006,221 describes an increase in GM-CSF and stem cell factor (SCF) expression following administration in mice. These results present intriguing questions about potential effects of *Polygonum multiflorum* extracts on stem cell activity, given that both GM-CSF and SCF are implicated as playing important roles in stem cell migration and mobilization, as described above.

Fucoidan.

Fucoidan is a sulfated fucan polysaccharide L-selectin agonist that was documented to promote the egress of HSCs from compartments in bone marrow into the peripheral blood stream upon intravenous injection, although this effect seemed unrelated to its stimulation of L-selectin (Frenette et al., 2000). Circulation of HSCs in the peripheral bloodstream is a critical step in promoting the stem cell regeneration and repair mechanisms in the body. As a sulfated fucan, fucoidan is found in various species of algae. Other sulfated fucans have also been found in animal species, such as echinoderms (e.g., sea urchins and sea cucumbers).

Despite in vivo data in animal models that demonstrate significantly elevated levels of HSCs following intravenous fucoidan administration, observations of positive clinical effects in human subjects are much more limited. Reported studies have shown that the percentage of HSCs expressing an important trafficking receptor, CXCR4, increased significantly following 4 days of oral fucoidan administration. (Irhimeh et al., 2007) However, only a slight change was observed in the absolute number of HSCs circulating in peripheral blood.

As described, fucoidan (also known as fucoidin or fucan-sulfate in the art) is a sulfated fucose polysaccharide L-selectin ligand. Selectin activity depends on important carbohydrate or polypeptide modifications such as sialylation, fucosylation, and sulfation. The presence of binding sites for sulfated fucans such as fucoidan on P- and L-Selectin has been demonstrated to be at least partially the mechanism by which fucoidan promotes detachment of HSCs from BM. (Frenette et al., 2000, 2461, Jensen et al., 2007, 190) Perhaps more significantly, sulfated fucans such as fucoidan, have been shown to displace SDF-1 sequestered on endothelial surfaces or bone marrow through completive binding to a heparin-binding domain present on SDF-1. Occupation of the heparin-binding site of SDF-1 by fucoidan prevents tethering to cell surfaces, thereby increasing circulating SDF-1 levels in plasma. (Sweeney et al., 2008) Without being bound by any particular theory, the enhanced levels of SDF-1 ligand in the bloodstream may thus promote egress of CXCR4 receptor expressing HSCs from the BM. (Sweeney et al., 2008) (FIG. 1C) Based on this model, the inventors hypothesized that L-selectin ligand, such as fucoidan, may possess a critical capacity to mobilize HSCs and oral administration of dietary supplements composed of fucoidan may best support natural regeneration and repair in the body.

Compelling in vivo data in animal models demonstrates significantly elevated levels of circulating HSCs following intravenous (IV) fucoidan administration in mice and primates, although significant drawbacks would present limitations for human therapeutic use. Recent reports have shown a dramatic 12-fold increase in levels of circulating HSCs, HSC progenitors and derivative cell types (including erythroid burst forming units, granulocyte, erythroid, macrophage, megakaryocyte colony forming units, granulocyte, erythroid, macrophage, and granulocyte macrophage colony-forming units) compared to untreated controls, 3 hours following injection of fucoidan (source unknown) into mice. Similar results of sustained elevation in levels of HSCs, HSCs progenitors and derivative cell types, were reported after daily injections for 3 days. (Sweeney et al., 2008) Injection of fucoidan in primates has also been demonstrated to increase HSCs and HSC-derivative levels by 11-26 fold after 6 hours after administration, with sustained elevation still observable up to 24 hours later. (Sweeney et al., 2000) Despite these positive observations, several challenges could impede therapeutic use of fucoidan in human subjects. The temporary and transitory effect of elevated HSCs circulating and bone marrow-derived stem cells may fail to fully realize the positive clinical benefits of stem cell regenerative and repair mechanisms, since sustained or repeated periods of elevation may be needed to enable stem cell homing and extravasation processes that underlie therapeutic stem cell activity. This limitation is further compounded in view of the difficulty and inconvenience of routinely administering IV injections.

Existing observations in human subjects are limited and available data on oral fucoidan administration in humans does not mirror the positive clinical effects of animal studies using IV injection. Reported studies by others have shown that the percentage of HSCs expressing an important trafficking receptor, CXCR4, increased significantly (45% to 90%) after 12 days of oral fucoidan administration (3 grams daily of 10% w/w or 75% w/w fucoidan extracts from *Undaria pinnatifida*). However, only a slight change (~12%) was observed in the absolute number of HSCs circulating in peripheral blood (maximal effect was 1.64 to 1.85 cells/pi after 4 days of fucoidan extract administration). (Irhimeh et al., 2007) Importantly, for therapeutic applications involving oral administration, fucoidan is capable of surviving acidic conditions in the stomach and does not demonstrate adverse side effects. (Irhimeh et al., 2007) This is consistent with reports that catalytic fucoidinase, which metabolizes fucoidan, is found only in marine interverbrates and not terrestrial mammals. (Berteau and Mulloy, 2003) This may provide an vital therapeutic benefit of high persistence and stability of an administered sulfated fucan, including fucoidan, for sustained therapeutic effect. It is particularly ideal for oral uses where diffusion into the bloodstream must first survive enzymatic processing in the mouth, esophagus, and intestines, in addition to the highly acidic conditions of the stomach.

The inventors have discovered that the source of fucoidan and appropriate dosing regimens are critical features for promoting HSC mobilization through oral fucoidan administration. Fucoidan is a member of the broader class of sulfated fucans, which are polysaccharides rich in L-fucose and obtained primarily from two sources: algae and marine invertebrates. Sulfated fucans obtained from these two sources differ greatly in composition and structure. This diversity of molecular structure further exists across fucoidans from different species of algae. While generally described as ~20,000 molecular weight polysaccharide composed of L-fucose, exact fucoidan structures depend in-part, on the source organism. As example, the most well-studied fucoidan from *F. vesculosus*, is reported to be composed primarily of L-fucose with $\alpha(1{\rightarrow}3)$ glycosidic bonds and sulfate groups at position 4, with sulfated fucose branches every 5 units. In contrast, fucoidan from a different algae, *Ascophylum nodosum*, has a large proportion of repeating $\alpha(1{\rightarrow}3)$ and $\alpha(1{\rightarrow}4)$ glycosidic bonds that alternate for oligosaccharide formation, possibly with few sulfated branching points as showing in nuclear magnetic resonance (NMR) studies (Berteau, 2003). In sum, fucoidans from different species are structurally distinct, heterogeneous and diverse.

The present invention provides new compositions and methods for providing a wide range of clinical and physiological benefits to a subject in need thereof by the administration of a mobilization agent. While not wishing to be bound by any particular theory, the inventors believe that the beneficial and other physiological results obtained through administration of the inventive compositions result from enhancing stem cell trafficking and migration that follows the administration of the mobilization agent.

In various embodiments, the mobilization agent comprises one or more components selected from the group including: *Polygonum multiflorum, Lycium Barabrum*, blue-green algae (e.g. *Aphanizomenon flos aquae* (AFA)), colostrum, mushroom polysaccharides (e.g., *Cordyceps sinensis, Hericium erinaceus* (Lion's mane), *Ganoderma lucidum* (Reishi)), fucoidan (optionally extracted from algaes, e.g., *Undaria pinnatifida, Chordaria cladosiphon* (*Limu*)), spirulina (e.g., *Arthrospira platensis, Arthrospira maxima*), analogs thereof, derivatives thereof, extracts thereof, synthetic or pharmaceutical equivalents thereof, fractions thereof, and combinations of any of the foregoing items. The mobilization agents may be combined together in one or more compositions or they may be administered or consumed separately as part of a regimen. They may have individual physiological effects, additive effects and/or synergistic effects with one another, such as serving as both a releasing agent and migration agent. In some embodiments, the mobilization agent is capable of functioning as a migration agent, promoting the process of a cell moving from the circulatory system into a tissue or organ. In some embodiments, the mobilization agent is capable of functioning as a releasing agent, promoting the release and egress of stem cells from a tissue of origin.

In one embodiment, a mobilization agent is administered to a subject, for example *Polygonum multiflorum*, though the subject may be provided a mixture of *Polygonum multiflorum*, and other mobilization agents. In some embodiments, the subject consumes and digests whole *Polygonum multiflorum* root, leaves, stem, seeds, fruits, and/or other plant parts. The whole *Polygonum multiflorum* root, leaves, stem, seeds, fruits, and/or other plant parts may be fresh, frozen, freeze-dried, dehydrated, fermented, or preserved in some other manner. Therefore, *Polygonum multiflorum*, as described herein, encompasses whole *Polygonum multiflorum* root, leaves, stem, seeds, fruits, and/or other plant parts. In other embodiments, the mobilization agent is an extract of *Polygonum multiflorum*, or an isolated component or compound extracted from *Polygonum multiflorum*, such as a compound found in a polysaccharide-rich fraction of *Polygonum multiflorum* extracts, or a fraction soluble in aqueous solutions, or a fraction soluble in organic solvents. *Polygonum multiflorum* can be provided alone as an isolated or purified substance, or may be part of a composition including a pharmaceutically acceptable carrier. In one embodiment, *Polygonum multiflorum* or extracts thereof is capable of functioning as a migration agent. In one embodiment, *Polygonum multiflorum* or extracts thereof is capable of functioning as a releasing agent.

Extracts of components found in *Polygonum multiflorum* include anthraquinones and derivatives, hydroxyl siltbenes, lecithin, chrysophanol, chrysophanic acid, chrysophanol anthrone, emodin, physcion, rhein, chrysophanic acid anthrone, resveratrol, piceid, 2,3,5,4'-tetrahydroxystilbene-2-O—O-D-glucopyranoside, 2,3,5,4'-tetrahydroxystilbene-2-O-β-D-glucopyranoside-2''-O-mo-nogalloyl ester, 2,3,5,4'-tetrahydroxystilbene-2-O-β-D-glucopyranoside-3''-O-monogalloyl ester, 2,3,5,4'-tetrahydroxystilbene-2-O-β-D-glucoside, gallic acid, catechin, epicatechin, 3-O-galloyl(–)-catechin, 3-O-galloyl(–)-epicatechin, 3-O-galloyl-procyanidin B-2,3,3'-di-O-galloyl-procyanidin B-2, and β-sitosterol.

The identity and nature (e.g., stability) of components in prepared *Polygonum multiflorum* extracts may vary depending on the method used for extraction. For example, water extraction is a leading method of exacting components from *Polygonum multiflorum*. However, certain components, such as anthraquinones and derivatives are very insoluble in water. Anthraquinones and derivatives are also insoluble in organic solvents at room temperature, but soluble in hot organic solvents (e.g., boiling temperature), such as methanol or ethanol. Similarly, 2,3,5,4'-tetrahydroxystilbene-2-O-β-d-glycoside is known to readily degrade in aqueous solutions in a temperature and pH dependent manner. (Ren et al. 2011) Therefore, it is understood that extracts of *Polygonum multiflorum* may be prepared according to any method known in the art. This includes, water extraction, organic solvent extraction (e.g., U.S. patent application Ser. No. 12/006,221), or combinations of such exemplary methods (e.g., admixtures). Examples of organic solvents that may be used include methanol, n-hexane, ethyl acetate, and n-butanol. Combinations of two or more water and/or organic solvents could be added together to generate additional partition layers for extracting different components in different partition layers. Similarly, extracts from *Polygonum multiflorum* may be prepared from fresh, unprocessed whole plants or parts thereof, or extracts may be prepared from processed *Polygonum multiflorum* whole plants or parts thereof. For example, processing may be performed by any known method in the art, one example being fermentation. Processing may improve bioavailability of the components in extracts from *Polygonum multiflorum*, such as through fermentation with bacteria such as *Lactobacillus* sp. (Park et al., 2011) or through addition of black beans.

In one embodiment, a mobilization agent is administered to a subject, for example a blue-green algae such as *Aphanizomenon flos aquae* (AFA), though the subject may be provided a mixture of blue-green algae and other mobilization agents. In some embodiments, the subject consumes and digests whole blue-green algae. Blue-green algae may be fresh, frozen, freeze-dried, dehydrated, or preserved in some other manner. In one embodiment, the mobilization agent is an extract of blue-green algae, or an isolated component or compound extracted from blue-green algae, such as a compound found in a polysaccharide-rich fraction of blue-green algae extract, or a compound in a water soluble compartment of an blue-green algae extract. Blue-green algae can be provided alone as an isolated or purified substance, or may be part of a composition including a pharmaceutically acceptable carrier. In one embodiment, blue-green algae is capable of functioning as a migration agent. In one embodiment, blue-green algae is capable of functioning as a releasing agent.

In one embodiment, a mobilization agent is administered to a subject, for example *Lycium barbarum*, though the subject may be provided a mixture of *Lycium barbarum* and other mobilization agents. In some embodiments, the subject consumes and digests whole *Lycium barbarum* berries. The berries may be fresh, frozen, freeze-dried, dehydrated, or preserved in some other manner. Therefore, *Lycium barbarum*, as described herein, encompasses both whole berry, or parts of the *Lycium barbarum* plant. In one embodiment, the mobilization agent is an extract of *Lycium barbarum*, or an isolated component or compound extracted from *Lycium barbarum*, such as a compound found in a polysaccharide-rich fraction of *Lycium barbarum* extract. *Lycium barbarum* can be provided alone as an isolated or purified substance, or may be part of a composition including a pharmaceutically acceptable carrier. In one embodiment, *Lycium barbarum* is capable of functioning as a migration agent. In one embodiment, *Lycium barbarum* is capable of functioning as a releasing agent.

In one embodiment, colostrum is administered to a subject, though the subject may be provided a mixture of colostrum and other mobilization agents. In some embodiments, the subject consumes and digests whole colostrum. The colostrum may be fresh, frozen, freeze-dried, dehydrated, or preserved in some other manner. In one embodiment, the mobilization agent is an extract of colostrum, or an isolated component or compound extracted from colostrum, such as a compound found in a protein-rich fraction of colostrum extract colostrum can be provided alone as an isolated or purified substance, or may be part of a composition including a pharmaceutically acceptable carrier. In one embodiment, colostrum is capable of functioning as a migration agent. In one embodiment, colostrum is capable of functioning as a releasing agent.

In one embodiment, mushroom or a blend of mushrooms is administered to a subject, though the subject may be provided a mixture of mushrooms and other mobilization agents. In some embodiments, the subject consumes and digests whole mushrooms. The mushrooms may be fresh, frozen, freeze-dried, dehydrated, or preserved in some other manner. In one embodiment, the agent is *Cordyceps sinensis* or an extract thereof. In one embodiment, the mobilization agent is *Ganoderma lucidum* or an extract thereof. In one embodiment, the mobilization agent is *Hericium erinaceus* or an extract thereof. Mushrooms can be provided alone as isolated or purified substances, or may be part of a composition including a pharmaceutically acceptable carrier. In one embodiment, mushrooms, *Cordyceps sinensis, Ganoderma lucidum*, and/or *Hericium erinaceus* is capable of functioning as a migration agent. In one embodiment, mushrooms, *Cordyceps sinensis, Ganoderma lucidum*, and/or *Hericium erinaceus* is capable of functioning as a releasing agent.

In one embodiment, algae is administered to a subject, though the subject may be provided a mixture of algae and other mobilization agents. In some embodiments, the subject consumes and digests whole algae. The algae may be fresh, frozen, freeze-dried, dehydrated, or preserved in some other manner. In one embodiment, the mobilization agent is *Chordaria cladosiphon* or an extract thereof. Algae can be provided alone as isolated or purified substances, or may be part of a composition including a pharmaceutically acceptable carrier. In one embodiment, algae, *Chordaria cladosiphon* is capable of functioning as a migration agent. In one embodiment, algae, *Chordaria cladosiphon* is capable of functioning as a releasing agent.

In one embodiment, spirulina is administered to a subject, though the subject may be provided a mixture of spirulina and other mobilization agents. In some embodiments, the subject consumes and digests whole spirulina. The spirulina may be fresh, frozen, freeze-dried, dehydrated, or preserved in some other manner. In one embodiment, the mobilization agent is *Arthrospira platensis, Arthrospira maxima*, or an extract thereof. *Spirulina* can be provided alone as an isolated or purified substance, or may be part of a composition including a pharmaceutically acceptable carrier. In one embodiment, spirulina is capable of functioning as a migration agent. In one embodiment, spirulina is capable of functioning as a releasing agent.

A method is described herein for enhancing stem trafficking by administering to a subject a therapeutically effective amount of *Polygonum multiflorum*.

In one embodiment, *Polygonum multiflorum*, is administered to a subject, though the subject may be provided a mixture of more than one ingredient. In some embodiments, the subject consumes and digests whole plant or parts of the plant. The *Polygonum multiflorum* may be fresh, frozen, freeze-dried, dehydrated, or preserved in some other manner.

In alternative embodiments, an extract of *Polygonum multiflorum* is provided or administered to the subject. In another embodiment, the *Polygonum multiflorum* encompasses both whole plant, parts of the plant, and extracts thereof. In another embodiment, the *Polygonum multiflorum* can be provided alone as an isolated or purified substance, or may be part of a composition including a pharmaceutically acceptable carrier. In another embodiment, the extract is an anthraquinone and/or derivative. In another embodiment, the extract is a hydroxylstilbene. In an alternative embodiment, whole *Polygonum multiflorum* plant is administered to the subject. In another embodiment, parts of *Polygonum multiflorum* plant are administered to the subject. In one embodiment, an extract of *Polygonum multiflorum* is administered to the subject.

The present invention further provides a pharmaceutical preparation. In one embodiment, the pharmaceutical preparation is 90%, 80%, 70%, 60%, 50%, 40%, 30%, 20%, 10%, 5%, or 1% w/w *Polygonum multiflorum* or extracts thereof.

The present invention further provides a dosing regimen. In one embodiment, the dosing regimen is dependent on the severity and responsiveness of a disease state to be treated, with the course of treatment lasting from a single administration to repeated administration over several days and/or weeks. In another embodiment, the dosing schedule is based on measurement of an active component accumulated in the body. In one embodiment, the active component is *Polygonum multiflorum* or extracts thereof. In another embodiment, the dosing regimen is dependent on the level of stem cell trafficking in the subject. In one embodiment, the dosing regimen is dependent on the activity of a releasing agent administered to a subject. In another embodiment, the dosing regimen is dependent on the number of circulating CD34+ HSCs in the peripheral blood stream of a subject. In another embodiment, the dosing regimen is dependent on the number of circulating bone marrow-derived stem cells in the peripheral blood stream of a subject. In one embodiment, the dosing regimen is 3 grams of *Polygonum multiflorum* or extracts thereof, administered daily. In another embodiment, the dosing regimen is 1 gram of *Polygonum multiflorum* or extracts thereof, administered daily. In another embodiment, the dosing regimen is 500 mg grams of *Polygonum multiflorum* or extracts thereof, administered daily. In one embodiment, the dosing regiment is 250 mg grams of *Polygonum multiflorum* or extracts thereof, administered daily. In another embodiment, the dosing regimen is 75 mg grams of *Polygonum multiflorum* or extracts thereof, administered daily. In another embodiment, the dosing regimen is 25 mg grams of *Polygonum multiflorum* or extracts thereof, administered daily.

A method is described herein for enhancing stem trafficking by administering to a subject a therapeutically effective amount of fucoidan.

In one embodiment, an algae, such as *Undaria pinnatifida*, is administered to a subject, though the subject may be provided a mixture of more than one algae. In some embodiments, the subject consumes and digests whole algae. The algae may be fresh, frozen, freeze-dried, dehydrated, or preserved in some other manner.

In alternative embodiments, an extract of the algae is provided or administered to the subject. In another embodiment, the algae encompasses both whole plant and/or extracts thereof. In another embodiment, the algae can be provided alone as an isolated or purified substance, or may be part of a composition including a pharmaceutically acceptable carrier.

In another embodiment, the extract is a highly sulfated, polyanionic soluble fiber. In one embodiment, the extract is an isolated fucoidan. In a different embodiment, the fucoidan is purified following isolation. In an alternative embodiment, a polysaccharide fraction is administered to the subject. In another embodiment, the highly sulfated, polyanionic soluble fiber is administered to the subject. In one, the isolated fucoidan is administered to the subject. In a different embodiment, the purified fucoidan is administered to the subject. In one embodiment, *Undaria pinnatifida* is capable of functioning as a releasing agent after administration to a subject.

The present invention further provides a pharmaceutical preparation. In one embodiment, the pharmaceutical preparation is 90%, 80%, 70%, 60%, 50%, 40%, 30%, 20%, 10%, 5%, or 1% w/w fucoidan.

A method is described herein for enhancing stem trafficking by administering to a subject a therapeutically effective amount of blue-green algae.

In one embodiment, blue-green algae, such as *Aphanizomenon flos aquae* (AFA) is administered to a subject, though the subject may be provided a mixture of more than one algae. In some embodiments, the subject consumes and digests whole algae. The AFA may be fresh, frozen, freeze-dried, dehydrated, or preserved in some other manner.

In alternative embodiments, an extract of AFA is provided or administered to the subject. In another embodiment, the AFA encompasses both whole plant, parts of the plant, and/or extracts thereof. In another embodiment, the AFA can be provided alone as an isolated or purified substance, or may be part of a composition including a pharmaceutically acceptable carrier. In another embodiment, the extract is water soluble compartment. In another embodiment, the extract is a polysaccharide rich compartment.

The present invention further provides a pharmaceutical preparation. In one embodiment, the pharmaceutical preparation is 90%, 80%, 70%, 60%, 50%, 40%, 30%, 20%, 10%, 5%, or 1% w/w AFA or extracts thereof.

The present invention further provides a dosing regimen. In one embodiment, the dosing regimen is dependent on the severity and responsiveness of a disease state to be treated, with the course of treatment lasting from a single administration to repeated administration over several days and/or weeks. In another embodiment, the dosing schedule is based on measurement of an active component accumulated in the body. In a certain embodiment, the active component is fucoidan. In one embodiment, the fucoidan is isolated from *Undaria pinnatifida* or extracts thereof. In another embodiment, the dosing regimen is dependent on the level of stem cell trafficking in the subject. In one embodiment, the dosing regimen is dependent on the activity of a releasing agent administered to a subject. In another embodiment, the dosing regimen is dependent on the number of circulating CD34+ HSCs in the peripheral blood stream of a subject. In another embodiment, the dosing regimen is dependent on the number of circulating bone marrow-derived stem cells in the peripheral blood stream of a subject. In one embodiment, the dosing regimen is 3 grams of fucoidan administered daily. In another embodiment, the dosing regimen is 1 gram of fucoidan administered daily. In another embodiment, the dosing regimen is 500 mg grams of fucoidan administered daily. In another embodiment, the dosing regimen is 75 mg grams of fucoidan administered daily. In one embodiment, the dosing regiment is 250 mg grams of fucoidan administered daily.

The present invention further provides a method of enhancing the trafficking of stem cells in a subject. In one embodiment, the level of trafficking of stem cells relates to the number of circulating CD34+ HSCs in the peripheral blood of a subject. In another embodiment, the level of trafficking of stem cells relates to the number of circulating bone marrow-derived stem cells in the peripheral blood of a subject.

In another embodiment, the method provided herein enhances the trafficking of stem cells in a subject, including administering a therapeutically effective amount of a composition containing one or more of the following components selected from the group including: *Polygonum multiflorum* or extracts thereof, *Lycium barbarum* or extracts thereof, blue-green algae or extracts thereof, colostrum or extracts thereof, spirulina or extracts thereof, *Arthrospira platensis* or extracts thereof, *Arthrospira maxima* or extracts thereof, fucoidan, *Chordaria cladosiphon* or extracts thereof, *Hericium erinaceus* or extracts thereof, *Ganoderma Lucidum* or extracts thereof, and/or *Cordyceps Sinensis* or extracts thereof, thereby enhancing the trafficking of stem cells in the subject. In one embodiment, enhancement of stem cell trafficking may be measured by assaying the response of stem cells to a particular dose of a composition containing one or more of the following components selected from the group including: *Polygonum multiflorum* or extracts thereof, *Lycium barbarum* or extracts thereof, blue-green algae or extracts thereof, colostrum or extracts thereof, spirulina or extracts thereof, *Arthrospira platensis* or extracts thereof, *Arthrospira maxima* or extracts thereof, fucoidan or extracts thereof, *Chordaria cladosiphon* or extracts thereof, *Hericium erinaceus* or extracts thereof, *Ganoderma Lucidum* or extracts thereof, and/or *Cordyceps Sinensis* or extracts thereof, thereby enhancing the trafficking of stem cells in the subject.

In another embodiment, the method provided herein enhances the trafficking of stem cells in a subject, including administering a therapeutically effective amount of a composition containing fucoidan. In one embodiment, enhancement of stem cell trafficking may be measured by assaying the response of stem cells to a particular dose of a composition containing fucoidan. In one embodiment, the fucoidan is from *Undaria pinnatifida* or extracts thereof.

The present invention further provides a method for enhancing the trafficking of stem cells in a subject, comprising administering a therapeutically effective amount of a mobilization agent, thereby increasing the release, circulation, homing and/or migration of stem cells in the subject, regardless of the route of administration.

The present invention further provides a method of inducing a transient decrease in the population of circulating stem cells, such as CD34+ stem cells. In one embodiment, administration of a mobilization agent results in the migration of stem cells from the circulation to tissues from about 1 to about 3 hours following administration. Circulating stem cells will leave the circulatory system, thus decreasing the number of circulating stem cells within the subject's body. Enhancement of stem cell migration may be measured by assaying the response of stem cells to a particular dose of *Polygonum multiflorum*. In one embodiment, providing a mobilization agent to a subject will enhance migration of that subject's stem cells within a certain time period, such as less than about 5 hours, less than about 4 hours, less than about 2 hours, or less than about 1 hour following administration. In other embodiments, the mobilization agent is *Lycium barbarum*, blue-green algae, colostrum, mushroom polysaccharides including *Cordyceps sinensis, Hericium erinaceus, Ganoderma lucidum*, fucoidan including *Chordaria cladosiphon*, spirulina, including *Arthrospira platensis*, and/or *Arthrospira maxima*.

In another embodiment, administration of an extract of *Polygonum multiflorum* increases the rate of homing of stem cells measured by a transient decrease in the number of circulating stem cells within the subject's body. In another embodiment, the percentage decrease in the number of circulating stem cells compared to a normal baseline may about 25%, about 50%, about 75%, or even about 100% as compared to a control. In one embodiment, the control is a base line value from the same subject. In another embodiment, the control is the number of circulating stem cells in an untreated subject, or in a subject treated with a placebo or a pharmacological carrier.

In another embodiment, administration of an extract of algae increases the rate of homing of stem cells measured by a transient decrease in the number of circulating stem cells within the subject's body. In another embodiment, the algae is *Chordaria cladosiphon*. In another embodiment, the percentage decrease in the number of circulating stem cells compared to a normal baseline may about 25%, about 50%, about 75%, or even about 100% as compared to a control. In one embodiment, the control is a base line value from the same subject. In another embodiment, the control is the number of circulating stem cells in an untreated subject, or in a subject treated with a placebo or a pharmacological carrier.

In another embodiment, administration of an extract of a mobilization agent increases the rate of homing of stem cells measured by a transient decrease in the number of circulating stem cells within the subject's body. The percentage decrease in the number of circulating stem cells compared to a normal baseline may be about 25%, about 50%, about 75%, or even about 100% as compared to a control. In one embodiment, the control is a base line value from the same subject. In another embodiment, the control is the number of circulating stem cells in an untreated subject, or in a subject treated with a placebo or a pharmacological carrier. In another embodiment, the administration of an extract of a mobilization agent leads to an increase in CXCR4 expression on circulating stem cells.

The present invention further provides a method of inducing a transient increase in the population of circulating stem cells, such as CD34+ stem cells following administration of *Polygonum multiflorum* or an extract thereof. In one embodiment, the stem cells are hematopoietic stem cells (HSGs). In another embodiment, the stem cells are bone marrow-derived stem cells. In one embodiment, enhancement of stem cell trafficking may be measured by assaying the response of stem cells to a particular dose of *Polygonum multiflorum* or an extract thereof. In one embodiment, providing *Polygonum multiflorum* or an extract thereof to a subject will enhance release of that subject's stem cells within a certain time period, such as less than 12 days, less than 6 days, less than 3 days, less than 2, or less than 1 days. In an alternative embodiment, the time period is less than 12 hours, 6 hours, less than about 4 hours, less than about 2 hours, or less than about 1 hour following administration. In another embodiment, the stem cells are bone marrow-derived stem cells.

In one embodiment, administration of *Polygonum multiflorum* or an extract thereof results in the release of stem cells into the circulation from about 2 to about 3 hours following administration. In another embodiment, released stem cells enter the circulatory system and increase the number of circulating stem cells within the subject's body. In another embodiment, the percentage increase in the number of circulating stem cells compared to a normal baseline may about 25%, about 50%, about 100% or greater than about 100% increase as compared to a control. In one embodiment, the control is a base line value from the same subject. In another embodiment, the control is the number of circulating stem cells in an untreated subject, or in a subject treated with a placebo or a pharmacological carrier.

The present invention further provides a method of inducing a transient increase in the population of circulating stem cells, such as CD34+ stem cells following administration of an algae extract. In one embodiment, the stem cells are hematopoietic stem cells (HSGs). In another embodiment, the stem cells are bone marrow-derived stem cells. In one embodiment, enhancement of stem cell trafficking may be measured by assaying the response of stem cells to a particular dose of algae extract. In one embodiment, providing algae extract to a subject will enhance release of that subject's stem cells within a certain time period, such as less than 12 days, less than 6 days, less than 3 days, less than 2, or less than 1 days. In an alternative embodiment, the time period is less than 12 hours, 6 hours, less than about 4 hours, less than about 2 hours, or less than about 1 hour following administration. In another embodiment, the stem cells are bone marrow-derived stem cells. In one embodiment, the algae extract is from *Undaria pinnatifida*.

In one embodiment, administration of algae extract results in the release of stem cells into the circulation from about 2 to about 3 hours following administration. In another embodiment, released stem cells enter the circulatory system and increase the number of circulating stem cells within the subject's body. In another embodiment, the percentage increase in the number of circulating stem cells compared to a normal baseline may about 25%, about 50%, about 100% or greater than about 100% increase as compared to a control. In one embodiment, the control is a base line value from the same subject. In another embodiment, the control is the number of circulating stem cells in an untreated subject, or in a subject treated with a placebo or a pharmacological carrier.

In some embodiments, the subject administered a mobilization agent is healthy. In other embodiments, the subject is suffering from a disease or physiological condition, such as immunosuppression, chronic illness, traumatic injury, degenerative disease, infection, or combinations thereof. In certain embodiments, the subject may suffer from a disease or condition of the skin, digestive system, nervous system, lymph system, cardiovascular system, endocrine system, or combinations thereof. In specific embodiments, the subject suffers from osteoporosis, Alzheimer's disease, cardiac infarction, Parkinson's disease, traumatic brain injury, multiple sclerosis, cirrhosis of the liver, any of the diseases and conditions described in the Examples below, or combinations thereof. Administration of a therapeutically effective amount of a mobilization agent may prevent, treat and/or lessen the severity of or otherwise provide a beneficial clinical benefit with respect to any of the aforementioned conditions, although the application of the inventive methods and use of the inventive mobilization agent is not limited to these uses. In various embodiments, the novel compositions and methods find therapeutic utility in the treatment of, among other things, skeletal tissues such as bone, cartilage, tendon and ligament, as well as degenerative diseases, such as Parkinson's and diabetes. Enhancing the release, circulation, homing and/or migration of stem cells from the blood to the tissues may lead to more efficient delivery of stem cells to a defect site for increased repair efficiency. The novel compositions and methods of the present invention may also be used in connection with gene therapeutic approaches.

The present invention further provides various compositions for administration to a subject. In one embodiment, the administration is topical, including ophthalmic, vaginal, rectal, intranasal, epidermal, and transdermal. In one embodiment, the administration is oral. In one embodiment, the composition for oral administration includes powders, granules, suspensions or solutions in water or non-aqueous media, capsule, sachets, tablets, lozenges, or effervescents. In another embodiment, the composition for oral administration further comprises thickeners, flavoring agents, diluents, emulsifiers, dispersing aids or binding agents.

Described herein are mobilization agents and methods of using mobilization agents towards promoting stem cell trafficking. Further described herein are migration agents and method of using migration agents to promote the process of stem cells moving from the circulatory system into a tissue or organ. Also described herein are releasing agents and methods of using releasing agents to promote egress of stem cells from a tissue of origin. Also described herein is a method of oral administration of fucoidan which results in a significant release of HSCs into peripheral blood circulation. The inventors have demonstrated effective administration of stem cell mobilization agents, thereby achieving a safe, convenient and effective method to enhance stem cell-related maintenance and repair in the human body. Although the pathology of stem cells is of great importance and interest, and pertains to the subject matter disclosed herein, the underlying scope of this invention is that the release, circulation, homing and/or migration of stem cells from the blood to tissues is of significance in repairing injured tissue and maintaining the vitality and health of existing tissue. Thus, the importance of developing methods and compositions for achieving this end are among the foci and aims of the present invention.

Accordingly, the present invention provides novel compositions and methods for, among other things, enhancing natural tissue healing and renewal in the body by supporting the trafficking of stem cells. Furthermore, the present invention provides novel compositions and methods for preventing, slowing or otherwise diminishing the development of health problems in a mammal by promoting trafficking of stem cells in the mammal. The compositions and methods disclosed herein may further increase regeneration of existing tissue by supporting the release, circulation, homing and/or migration of stem cells into tissue, therefore supporting the process of tissue repair.

EXAMPLES

The following examples are provided to better illustrate the claimed invention and are not to be interpreted as limiting the scope of the subject matter. To the extent that specific materials are mentioned, it is merely for purposes of illustration and is not intended to limit the invention. One skilled in the art may develop equivalent means, compositions or reactants without the exercise of inventive capacity and without departing from the scope of the present invention.

Example 1

Production and Preparation of *L. barbarum*

Polysaccharides from *Lycium barbarum* were prepared by the method of Luo et al. (2004). The dried fruit samples (100 g) were ground to fine powder and put in 1.5 l of boiling water and decocted for 2 h by a traditional method for Chinese medicinal herbs. The decoction was left to cool at room temperature, filtered and then freeze-dried to obtain crude polysaccharides.

The dried crude polysaccharides were refluxed three times to remove lipids with 150 ml of chloroform:methanol solvent (2:1) (v/v). After filtering the residues were air-dried. The result product was extracted three times in 300 ml of hot water (90° C.) and then filtered. The combined filtrate was precipitated using 150 ml of 95% ethanol, 100% ethanol and acetone, respectively. After filtering and centrifuging, the precipitate was collected and vacuum-dried, giving desired polysaccharides (13 g). The content of the polysaccharides was measured by phenolsulfuric method (Masuko et al., 2005). Result showed that the content of the polysaccharides in the extract may reach 97.54%.

Example 2

Stem Cells Migrate Following *Lycium barbarum* Consumption

Figure 2:
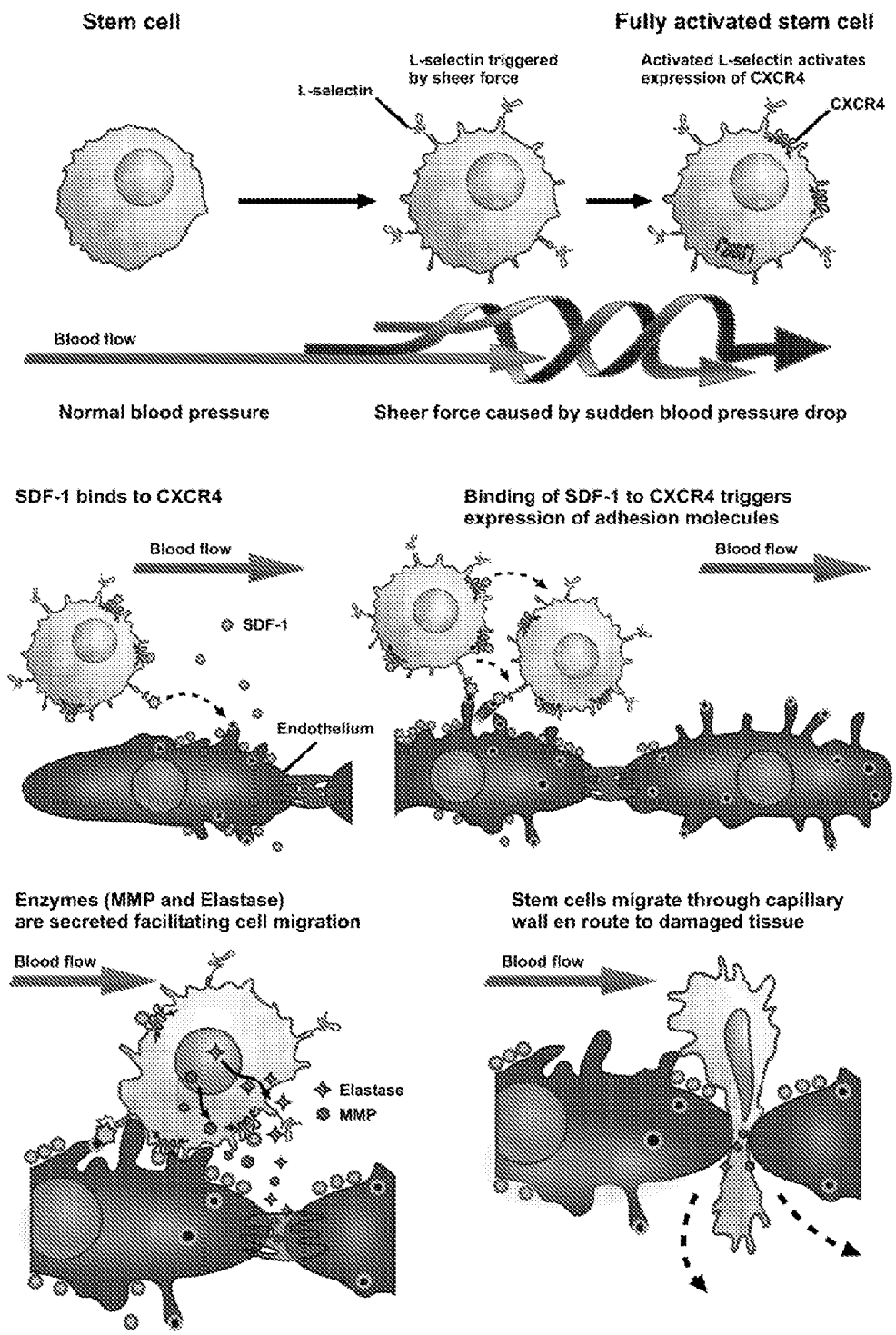
FIG. 2 shows a schematic illustration of the steps involved in the migration of a stem cell, underscoring the role of CXCR4, in accordance with an embodiment of the present invention.
Figure 5:
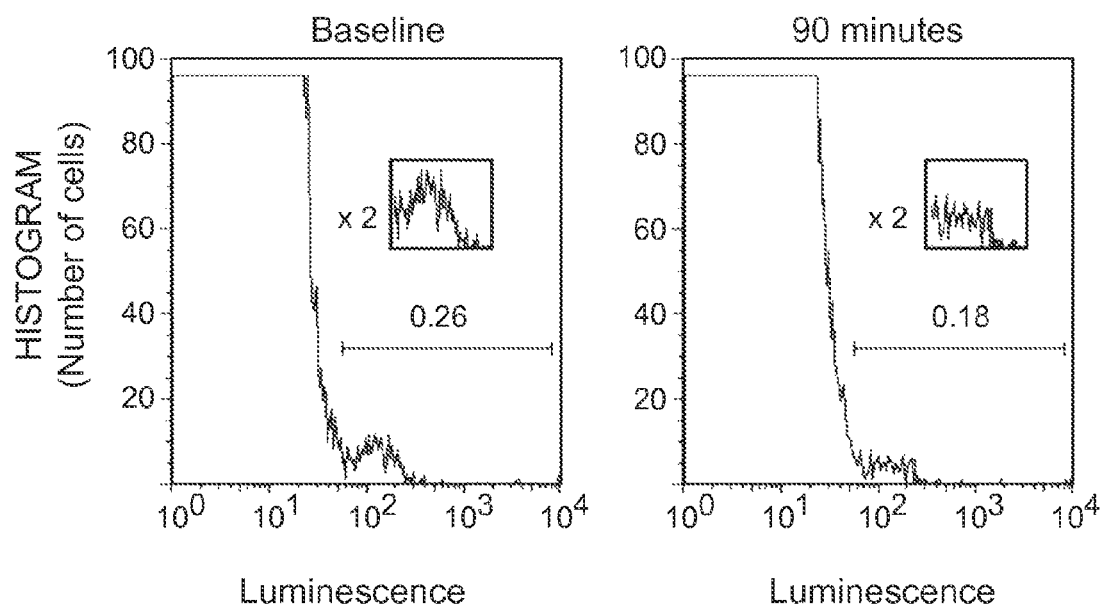
FIGS. 5A, 5B and 5C are flow cytometry profiles of blood samples showing the proportions of CD34+ lymphocytes from the peripheral blood of a human volunteer after ingestion of *L. barbarum*, colostrum and mushroom polysaccharides, respectively, in accordance with an embodiment of the present invention. The X axis displays fluorescence intensity of the stem cell marker. The M1 marker indicates events showing positivity for the stem cell marker CD34.

Consumption of *Lycium barbarum*, or compounds thereof, enhances recruitment and migration of CD34+ stem cells (see FIG. 2 for a diagram of stem cells entering the circulatory system).

Healthy human volunteers were identified, and the proportion of CD34+ cells was evaluated in the peripheral blood (circulating CD34+ cells) of each person prior to consumption of *Lycium barbarum* and hourly for up to 4 hours after consumption. The volunteers were instructed to limit physical and mental activity for a time before and after consumption of *Lycium barbarum*.

Each person was provided 5 grams of dried *Lycium barbarum* or 1 gram of polysaccharide extracted from *Lycium barbarum*. Red blood cells in whole blood samples obtained from each volunteer were lysed using FACS lysing solution (Beckton Dickenson, San Jose, Calif.). The remaining cells were washed and stained with monoclonal antibody HPCA-2 conjugated with fluorescein isothiocyanate. Samples were fixed in 1% formalin and analyzed by flow cytometry using a FacsCalibur flow cytometer (Becton Dickenson, San Jose, Calif.) and CellQuest software (Becton Dickenson, San Jose, Calif.).

Figure 6:
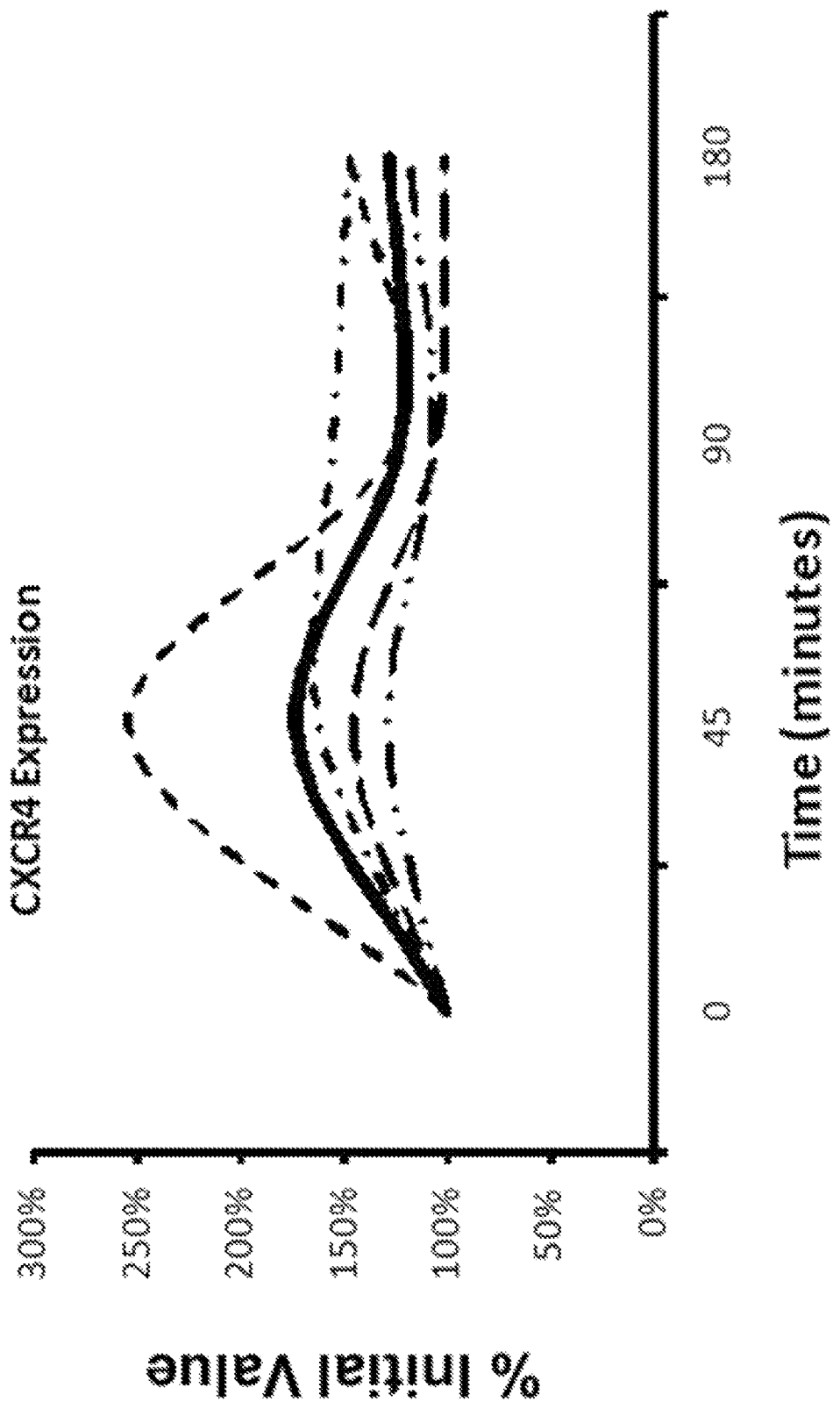
FIG. 6 is a graph illustrating the expression of CXCR4 molecules on the surface of CD34+ circulating stem cells before and after consumption of LB, Col, and mushroom polysaccharides, in accordance with an embodiment of the present invention.

FIG. 3A illustrates that consumption of *Lycium barbarum* triggered a strong transient decrease in circulating stem cells. Specifically, the X-axis shows the time course of a typical experiment after *Lycium barbarum* ingestion, expressed as a percentage of the control level. At the time of ingestion, the proportion of circulating CD34+ cells is the same as the control. The peak decrease in circulating CD34+ cells was observed at about 1-2 hours after consumption. At this time point, the number of circulating CD34+ cells was decreased by 30% below the control value. By 4 hours after *Lycium barbarum* ingestion, the circulating CD34+ cells had returned to the baseline value. The decrease in the number of circulating stem cells was accompanied by an increase in the expression of CXCR4 on the membrane of circulating stem cells (FIG. 6).

Therefore, *Lycium barbarum* (or a biological component of *Lycium barbarum*) can enhance the migration of endogenous stem cells (e.g. CD34+ cells) from the circulation to tissues. Consumption of *Lycium barbarum* (or a biological component of *Lycium barbarum*) triggers the migration CD34+ stem cells (e.g., see FIG. 3), thereby demonstrating the efficacy of *Lycium barbarum* as a migration agent.

Example 3

Stem Cells Migrate Following Colostrum Consumption

As in Example 2, and with reference to FIG. 3B, administration of colostrum results in stem cell migration.

Example 4

Stem Cells Migrate Following Mushroom Consumption

As in Example 2, and with reference to FIG. 4, administration of a polysaccharide rich fraction of mushroom (*Cordyceps sinensis, Ganoderma lucidum, Hericium erinaceus*) results in stem cell migration.

Example 5

Stem Cells Migrate Following Fucoidan or *Spirulina* Consumption

Figure 7:
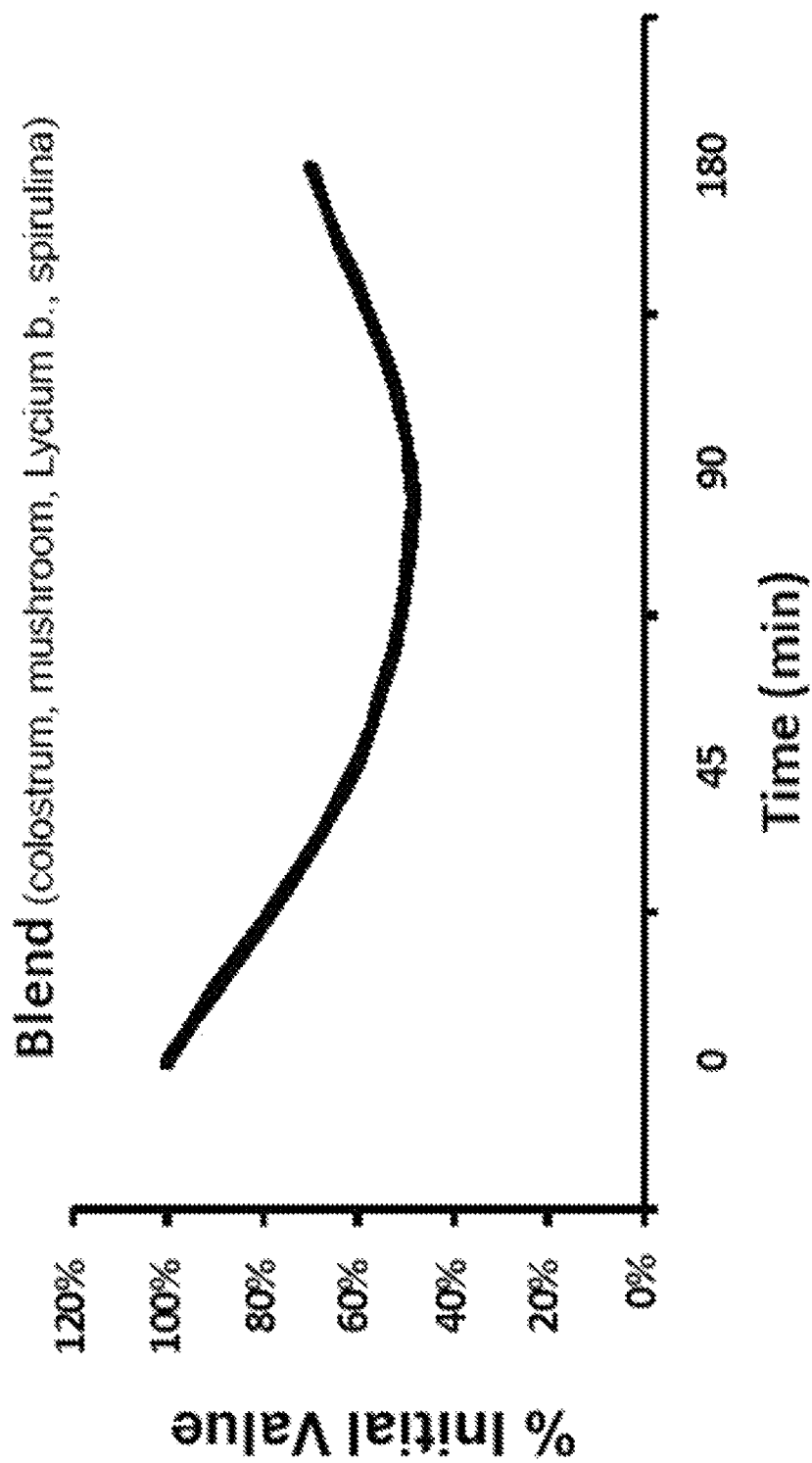
FIG. 7 provides a graph illustrating a typical time course of stem cell migration in the human body after consumption of *Lycium barbarum*, colostrum, spirulina and a polysaccharide rich fraction of mushroom (*Cordyceps sinensis, Ganoderma lucidum, Hericium erinaceus*), in accordance with an embodiment of the present invention.

As in Example 2, administration of fucoidan from algae seaweeds such as *Chordaria cladosiphon* promotes certain beneficial results that may ultimately, albeit indirectly, assist with stem cell migration. For example, consumption of fucoidan from *Chordaria cladosiphon* resulted in a decrease in the number of circulating CD34+HSCs (FIG. 9), suggesting an effective role in supporting stem cell migration. As in Example 2, administration of spirulina results in stem cell migration (FIG. 4B), and administration of spirulina with *Lycium barbarum*, colostrum and mushrooms also results in stem cell migration (FIG. 7).

Example 6

Stem Cells Migrate Following Consumption of a Blend of LB, *Colostrum, Spirulina* and Mushroom Compositions including the following components listed in Table 1 are provided to mammalian subjects. Administration of these compositions results in stem cell migration.

TABLE 1

|  | Composition 1 mg/dose | Composition 2 mg/dose | Composition 3 mg/dose | Composition 4 mg/dose |
|---|---|---|---|---|
| *Lycium barbarum* (Goji extract) | 500 | 1,000 | 1,500 | 2,000 |
| Colostrum (Fractionated) | 75 | 150 | 225 | 300 |
| *Spirulina* | 75 | 150 | 225 | 300 |
| Mushroom | 250 | 500 | 750 | 1,000 |
| *Hericium erinaceus* | 83 | 166 | 249 | 332 |
| *Ganoderma Lucidum* | 83 | 166 | 249 | 332 |
| *Cordyceps Sinensis* | 83 | 166 | 249 | 332 |

Example 7

Stem Cells from Bone Marrow Populate Multiple Distant Tissues

A murine model is chosen to evaluate how a mixture of LB, colostrum and mushroom can stimulate stem cell migration into tissues, and therefore populate and repair distant tissues of the body.

Male mice are selected as bone marrow donor animals, while all recipient mice are females. Female recipients are sub-lethally irradiated prior to injection of GFP+ male bone marrow cells into their tail veins. Two groups of mice are evaluated. The first group of 20 animals are sub-lethally irradiated, injected with bone marrow, and put on normal feed. The second group of 20 animals are also sub-lethally irradiated, receive male bone marrow, and are fed a diet of normal feed plus a mixture of LB, colostrum and mushroom. Incorporation of GFP+ cells is examined in the brain, heart muscle, muscles, liver, pancreas, sections of small intestine, and lung tissue These data document the extent to which a diet containing a mixture of LB, colostrum and mushroom promotes the homing and migration of bone marrow stem cells to various tissues.

Example 8

Increased Stem Cell Repopulation of Traumatized Tissue

A murine model is chosen to evaluate how a mixture of LB, colostrum and mushroom can stimulate stem cell migration into tissues, and therefore populate and repair distant tissues of the body.

Male mice are selected as bone marrow donor animals, while all recipient mice are females. Female recipients are sub-lethally irradiated prior to injection of GFP+ male bone marrow cells into their tail veins. Two groups of mice are evaluated. The first group of 20 animals are sub-lethally irradiated, injected with bone marrow, and put on normal feed. The second group of 20 animals are also sub-lethally irradiated, receive male bone marrow, and are fed a diet of normal feed plus a mixture of LB, colostrum and mushroom.

After bone marrow transplant and a few days prior to the initiation of the feeding trial, animals are subjected to an injury such as injection of cardiotoxin in the tibialis muscle, triggering of heart attack by ligation of coronary artery, punch of the skin, laser-induced stroke, or other injuries. The recovery of mice in both groups is monitored during 6 weeks using whole body fluorescence imaging. After 6 weeks, the animals are sacrificed and the injured tissue is analyzed to assess the extent of tissue repair. Incorporation of GFP+ cells will also be examined in the brain, heart muscle, muscles, liver, pancreas, sections of small intestine, and lung tissue These data document the extent to which a diet containing a mixture of LB, colostrum and mushroom promotes the homing and migration of bone marrow stem cells to injured tissues, therefore enhancing the process of tissue repair and healing.

Example 9

General Study Design for Fucoidan as a Stem Cell Mobilization Agent

Two consumables were tested in human subjects: fucoidan extracted from *Undaria* and a placebo. Peripheral venous blood samples were obtained from healthy human volunteers between 20 and 45 years of age upon informed consent. Blood and bone marrow samples were obtained under aseptic conditions and processed immediately. One gram of fucoidan or placebo was given to volunteers with 4-6 oz water. Appearance of the placebo was identical to that of the fucoidan and consisted of tan-dyed, finely ground potato flakes encapsulated in vegetable capsules.

Example 10

In Vivo Study Design

The following exclusion criteria were used: under 20 or over 65 years of age, pregnancy, severe asthma and allergies requiring daily medication, any known chronic illness or previous/current venereal disease, frequent recreational drug use, and impaired digestive function (including previous major gastrointestinal surgery). Three volunteers were scheduled on two study days one week apart. Testing was always performed at the same time of the day (8-11 a.m.) to minimize the effect of circadian fluctuations. Due to the interference from stress with the release vs. homing of other types of lymphocytes, effort was taken to minimize any physical and mental stress during testing. In addition, on each study day, volunteers were instructed to complete a questionnaire aimed at determining any exceptional stress related circumstances that might affect the person on that particular study day. Predetermined criteria for exclusion from final analysis included significant lack of sleep and severe anxiety. After completing the questionnaire, volunteers were instructed to remain quiescent for 4 h, comfortably seated in a chair. After the first hour, the baseline blood sample was drawn. Immediately after drawing the baseline sample, a consumable was provided. Blood samples were later drawn 60, 90 and 180 min after ingestion of the consumable. At each time point, 5 ml of blood was drawn into heparin, and 2 ml blood was drawn into EDTA. The blood vials were placed on a rocking plate until use.

Example 11

Measurement of Stem Cell Populations Using FACS Sorting

The blood drawn into EDTA was used for obtaining a complete blood count (CBC) with differential, using a Coulter counter (Micro Diff II, Beckman Coulter). All CBCs were performed within an hour of drawing the sample. All CBCs were performed in triplicate. The heparinized blood was used for purification of the PBMC fraction by gradient centrifugation and processed for immunostaining and flow cytometry. The stem cell markers CD34-FITC (clone 8G12, BD BioSciences, San Jose, Calif., USA) and CD133-PE (Miltenyi Biotech, Auburn, Calif., USA) were used for two color immunofluorescence. Staining of all samples with CD34-FITC/CD133-PE was performed in triplicate. IgG1-FITC and IgG1-PE isotype controls (BD BioSciences) were used in parallel samples. Separate, positive control samples for each donor included CD45-FITC and CD14-PE. Stained PBMC were fixed in 1% formalin and acquired by flow cytometry immediately. Files of 200,000 events were collected on each triplicate sample. The percent CD34+ CD133−, CD34+CD133+, and the CD34−CD133+ subsets were analyzed separately and were analyzed again after multiplying with the lymphocyte cell counts, as obtained from the average of the triplicate lymphocyte counts obtained by the CBC differential count.

Example 12

Increase in CD34+HSCs Circulating in Peripheral Blood Following Oral Administration of Fucoidan from *Undaria pinnatifida*

Figure 8:
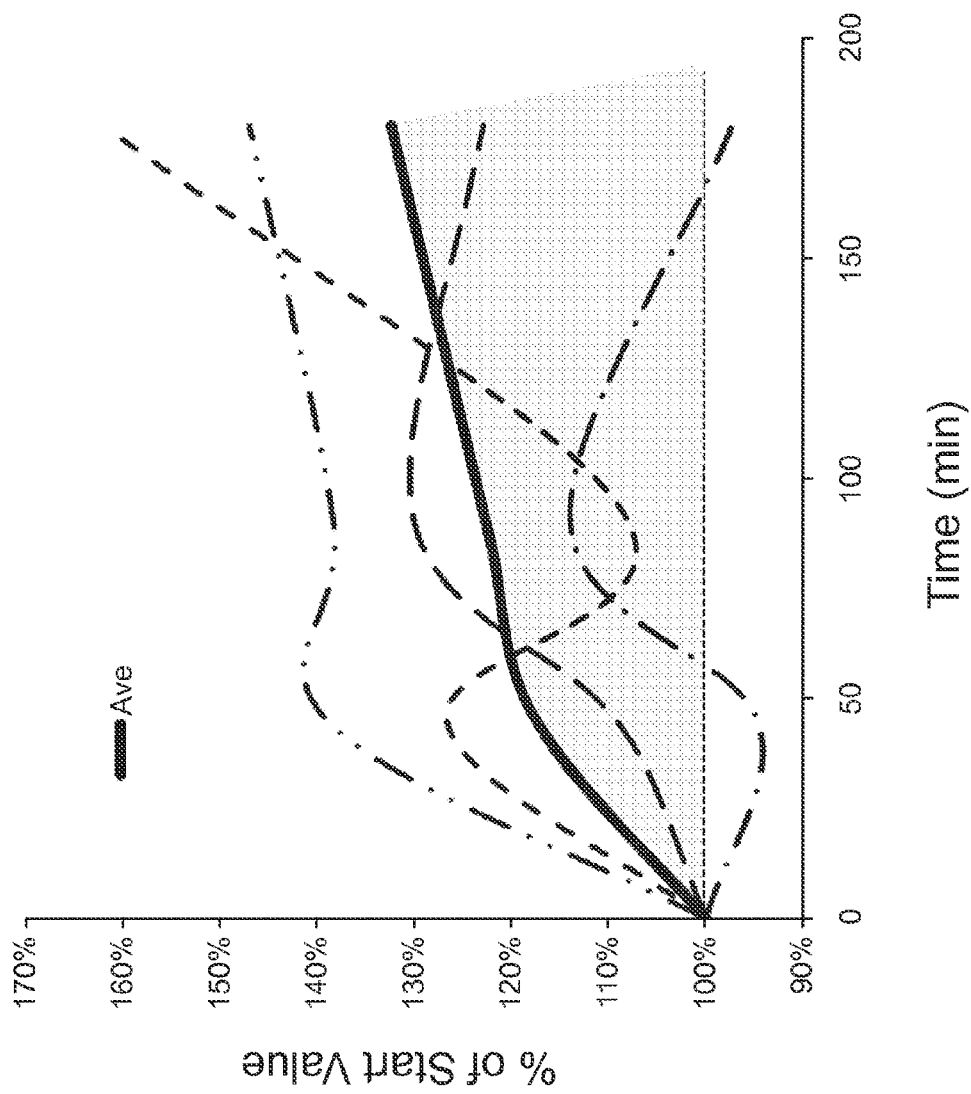
FIG. 8 depicts changes in circulating CD34+ hematopoietic stem cells in human volunteers following oral administration of fucoidan extracted from *Undaria pinnatifida* in accordance with various embodiments of the present invention. Baseline levels of peripheral blood stem cells were quantified in volunteers. Volunteers then ingested 250 mg of fucoidan extracted from *Undaria pinnatifida*. The levels of stem cells were subsequently measured at 45, 90 and 180 minutes. The number of circulating stem cells increased on average by 17%, 23% (P<0.02) and 32% (P<0.02), respectively.

The inventors tested oral administration of fucoidans from several different algae species for their potential to effectuate HSC mobilization in the peripheral bloodstream of human subjects. Fucoidan from one species, *Undaria pinnatifida*, resulted in a significant elevation in the number of circulating CD34+HSCs, with increases of 17%, 23% ($P<0.02$) and 32% (($P<0.02$) occurring at 45, 90 and 180 minute measurement intervals, thereby demonstrating efficacy as a releasing agent. (FIG. 8) To the best of the inventors' knowledge, this is the most significant increase reported in the literature and further, is a notable improvement over the previously reported 12% increase after 14 days in Irimeh et al., which also tested oral administration of fucoidan from *Undaria pinnatifida*. Importantly, Irimeh et al. reported 3 gram of fucoidan administered daily, whereas the inventors achieved improved results using a 250 mg dosage regime. This highlights an important role for applying a specific dosage when orally administering fucoidan to promote release and circulation of CD34+ HSCs. Furthermore, a lower dosage may permit longer-term patient use, such as routine daily administration, whereas higher dosages may not be compatible with repeated and/or routine use.

Example 13

Decrease in CD34+HSCs Circulating in Peripheral Blood Following Oral Administration of Fucoidan from *Chordaria cladosiphon*

Figure 9:
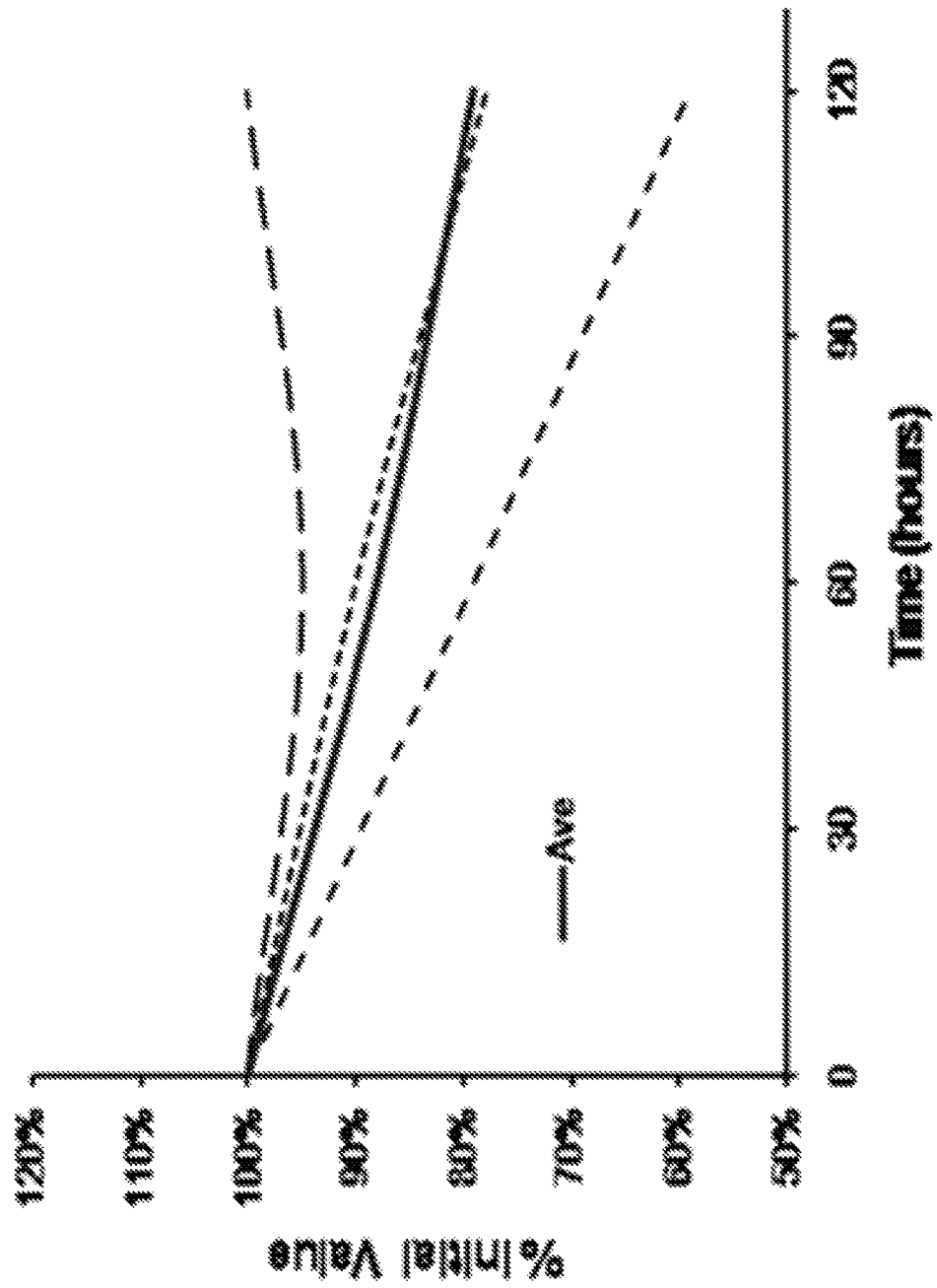
FIG. 9 depicts the results of consuming fucoidan from algae species, *Chordaria cladosiphon* in accordance with various embodiments of the present invention. Consumption of 250 mg of fucoidan from *Chordaria cladosiphon* gave an average decrease in the number of circulating stem cells under the same conditions.

Extending these observations, the inventors discovered that fucoidan from several other algae species, including *Chordaria cladosiphon*, failed to elevate the circulating number of CD34+ HSCs in human subjects (FIG. 9). Despite application of several dosage regimes, including the effective 250 mg dosage of fucoidan from *Undaria pinnatifida* as described above, fucoidan from *Chordaria cladosiphon* resulted in a decrease in the number of circulating CD34+ HSCs, probably consequent to an increase in CXCR4 expression on the surface of circulating HSCs. These results reflect the complex interplay between the exact source of fucoidan and identifying an effective therapeutic dose. Consumption of 250 mg of this fucoidan from *Chordaria cladosiphon* gave an average decrease in the number of circulating stem cells (FIG. 3) using the same fucoidan preparation methods and administered under the same conditions in volunteers, thereby demonstrating an effective role in supporting migration of stem cells.

These results are consistent with earlier reports that fucoidan from different sources diverge in structure-activity relationships. Fucoidan fractions from *A. nodosum* and *Pelvetia canculata* have been reported to possess anti-coagulant activity through the tri-sulfated disaccharide heparin-like motif involved in HSC mobilization. Particularly notable was the report that sulfation patterns correlated with their anticoagulant activities. A similar molecule from the family of galactans, 3-linked, regularly 2-O-sulfated galactan, possesses anticoagulant activity not found in a corresponding 3-linked, regularly 2-O-sulfated fucan. (Berteau and Mulloy, 2003; Mourão and Pereira, 1999; Pereira et al., 2002) These reports about anti-coagulant activity and the inventors' observations about HSC mobilization clearly demonstrate that the structure-activity relationships of sulfated fucans, including fucoidan, is not the result from generic features, such as charge density from the presence or absence of certain chemical groups. Instead, biological activity depends critically on the exact structure of the polysaccharide. Necessarily, the different structural fucoidans from distinct species of algae is expected to provide a complex range of efficacies for various therapeutic applications, including HSC mobilization. As described above, this will also require establishing effective therapeutic doses, which may vary when using fucoidans from different species.

Example 14

Various Methods of Preparing *Polygonum multiflorum*

A simple preparation of *Polygonum multiflorum* may be prepared by obtaining a portion of the fresh plant root that is then washed in water, cleaned, cut into pieces, and then dried. For example, crushed root may be diluted in water in a 12:1 extract as a simple preparation.

In another method of preparation, the *Polygonum multiflorum* may be frozen overnight at low temperatures (e.g., −70° C., −20° C., or 0° C.), and then crushed to form a solid powder, which can be dried at room temperature, or placed in a vacuum evaporator to remove moisture.

The solid powder may be immersed in water, an aqueous solution, or an organic solvent to extract different components from *Polygonum multiflorum*. As described, certain high temperatures (e.g., boiling) of organic solvents (e.g., ethanol or methanol) promote extraction of components, such as anthraquinones and derivatives, as they are otherwise insoluble in water, and room temperature organic solvents. Likewise, applying low temperature (4° C.) for extraction of aqueous fractions promotes stable isolation of certain components, such as hydroxyl stilbenes, as certain hydroxyl stilbenes degrade in a pH or temperature dependent manner. Again, immersion in water, an aqueous solution, or an organic solvent may be followed by drying at room temperature, or placed in a vacuum evaporator to remove moisture. Solid powders may be lyophilized at various stages in order to aid solubility.

Example 15

General Study Design for *Polygonum multiflorum* as a Stem Cell Mobilization Agent Two consumables were tested in human subjects: *Polygonum multiflorum* extracts and a placebo. Peripheral venous blood samples were obtained from healthy human volunteers between 20 and 45 years of age upon informed consent. Blood and bone marrow samples were obtained under aseptic conditions and processed immediately. One gram of as 12:1 preparation of *Polygonum multiflorum* extracts or placebo was given to volunteers with 4-6 oz water. Appearance of the placebo was identical to that of the *Polygonum multiflorum* extracts and consisted of tan-dyed, finely ground potato flakes encapsulated in vegetable capsules. As described in Example 10, the following exclusion criteria were used: under 20 or over 65 years of age, pregnancy, severe asthma and allergies requiring daily medication, any known chronic illness or previous/current venereal disease, frequent recreational drug use, and impaired digestive function (including previous major gastrointestinal surgery). Seven volunteers were scheduled on two study days one week apart. Testing was always performed at the same time of the day (8-11 a.m.) to minimize the effect of circadian fluctuations. Volunteers were instructed to remain quiescent for 4 h, comfortably seated in a chair. After the first hour, the baseline blood sample was drawn. Immediately after drawing the baseline sample, a consumable was provided. Blood samples were later drawn 60 and 120 min after ingestion of the consumable. At each time point, 5 ml of blood was drawn into heparin, and 2 ml blood was drawn into EDTA. The blood vials were placed on a rocking plate until use.

Example 16

Stem Cells Mobilize Following Consumption of *Polygonum multiflorum* Alone, or when Included in a Blend of *Polygonum multiflorum*, *Lycium barbarum*, Fucoidan, Colostrum, *Spirulina* and Mushroom

*Polygonum multiflorum* was shown to trigger a modest increase in the number of circulating stem cells by 13±6% (n=7) (p<0.05). The increase exceeded 25% in 2 or the participants. The results are shown in FIG. 10.

Example 17

Stem Cells Mobilize Following Consumption of a Blend of *Polygonum multiflorum*, *Lycium barbarum*, Fucoidan, Colostrum, *Spirulina* and Mushroom In addition Various compositions containing stem cell mobilization agents, including *Polygonum multiflorum* may be prepared, including the following components listed in Table 2 or 3. Administration of these compositions results in stem cell migration and/or mobilization.

TABLE 2

|  | Composition 5 mg/dose | Composition 6 mg/dose | Composition 7 mg/dose | Composition 6 mg/dose |
| --- | --- | --- | --- | --- |
| *Polygonum multiflorum* | 250 | 250 | 500 | 1,000 |
| *Lycium barbarum* (Goji extract) | 250 | 250 | 500 | 0 |
| Blue-green algae (*Aphanizomenon flos aquae* (AFA)) | 25 | 100 | 250 | 0 |
| Fucoidan | 0 | 400 | 500 | 1,000 |
| Colostrum (Fractionated) | 50 | 150 | 125 | 300 |
| *Spirulina* | 75 | 150 | 125 | 300 |

TABLE 2-continued

|  | Composition 5 mg/dose | Composition 6 mg/dose | Composition 7 mg/dose | Composition 6 mg/dose |
|---|---|---|---|---|
| Mushroom | 250 | 500 | 750 | 1,000 |
| Hericium erinaceus | 83 | 166 | 249 | 332 |
| Ganoderma Lucidum | 83 | 166 | 249 | 332 |
| Cordyceps Sinensis | 83 | 166 | 249 | 332 |

TABLE 3

|  | Composition 9 mg/dose | Composition 10 mg/dose | Composition 11 mg/dose | Composition 12 mg/dose |
|---|---|---|---|---|
| Polygonum multiflorum | 25 | 400 | 300 | 400 |
| Lycium barbarum (Goji extract) | 0 | 0 | 0 | 0 |
| Blue-green algae (Aphanizomenon flos aquae (AFA)) | 585 | 115 | 200 | 585 |
| Fucoidan | 115 | 285 | 100 | 115 |
| Colostrum (Fractionated) | 0 | 50 | 100 | 0 |
| Spirulina | 0 | 50 | 100 | 0 |
| Mushroom | 375 | 200 | 450 | 0 |
| Hericium erinaceus | 0 | 66 | 150 | 0 |
| Ganoderma Lucidum | 0 | 66 | 150 | 0 |
| Cordyceps Sinensis | 375 | 66 | 150 | 0 |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the sources of stem cell mobilization agents, the methods of preparing, isolating, or purifying stem cell mobilization agents, analogs and derivatives thereof, methods of treating various disease and/or conditions using stem cell mobilization agents, analogs and derivatives thereof, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

Abedi M., Greer D., Colvin G., Demers D., Dooner M., Harpel J., Pimentel J., Menon M., and Quesenberry P., Tissue injury in marrow transdifferentiation Blood Cells, Molecules and Diseases 2004 32, 42-46

Andriole G., Mule J., Hansen C., Linehan W., Rosenberg S., Evidence that lymphokine-activated killer cells and natural killer cells are distinct based on an analysis of congenitally immunodeficient mice. Journal of Immunology 1985 135, 2911-2913.

Adams G. and Scadden D., The hematopoietic stem cell in its place. Nature Immunology 2006 7, 333-337.

Asahara T., Masuda H., Takahashi T., Kalka C., Pastore C., Silver M., Kearne M., Magner M., and Isner J., Bone Marrow Origin of Endothelial Progenitor Cells Responsible for Postnatal Vasculogenesis in Physiological and Pathological Neovascularization. Circulation Research 1999 85, 221-228.

Barker N., van de Wetering M, Clevers H. The intestinal stem cell. Genes and Development 2008 22, 1856-64.

Bertea O. and Mulloy B., Sulfated fucans, fresh perspectives: structures, functions, and biological properties of sulfated fucans and an overview of enzymes active toward this class of polysaccharide. Glycobiology 2003 13, 29-40.

Branski L., Gauglitz G., Herndon D., and Jeschke M., A review of gene and stem cell therapy in cutaneous wound healing. Burns, Jul. 4. 2008.

Burke Z D, Thowfeequ S, Peran M, Tosh D. Stem cells in the adult pancreas and liver. Biochemistry Journal 2007 404, 169-78.

Dezawa M., Ishikawa H., Hoshino M., Itokazu Y., and Nabeshima Y., Potential of bone marrow stromal cells in applications for neuro-degenerative, neuro-traumatic and muscle degenerative diseases. Current Trends in Neuropharmacology 2005 3, 257-66.

Drapeau C., Cracking the Stem Cell Code, Sutton Hart Press (Portland, Oreg. 2010)

Fraser J., Schreiber R., Zuk P., and Hedrick M., Adult stem cell therapy for the heart. International Journal of Biochemistry & Cell Biology 2004 36, 658-666

Frenette P. and Weiss L., Sulfated glycans induce rapid hematopoietic progenitor cell mobilization:evidence for selectin-dependent and independent mechanisms. Hemostasis, Thrombosis, and Vascular Biology 2000 96, 2460-2468.

Hidalgo, A., Sanz-Rodriguez F., Rodriguez-Fernandez J., Albella B., Blaya C., Wright N., Cabañ as C., Prósper F., Gutierrez-Ramos J., Teixidó J., Chemokine stromal cell-derived factor-1 alpha modulates VLA-4 integrin-dependent adhesion to fibronectin and VCAM-1 on bone marrow hematopoietic progenitor cells. Experimental. Hematology, 2001 29, 345-55;

Irhimeh M., Fitton J., and Lowenthal R., Fucoidan ingestion increases the expression of CXCR4 on human CD34+ cells. Experimental Hematology 2007 35, 989-994.

Jang Y., Collector M., Baylin S., Diehl A., and Sharkis S., Hematopoietic stem cells convert into liver cells within days without fusion. Nature Cell Biology 2004, 6, 532-529.

Jensen, G. and Drapeau C., The use of in situ bone marrow stem cells for the treatment of various degenerative diseases. Medical Hypotheses 2002 59, 422-428.

Jensen, G., Hart A., Lue A., Drapeau C., Gupta N., Scaehffer D., and Cruickshank J. Mobilization of human CD34+ CD133+ and CD34+CD133- stem cells in vivo by consumption of an extract from Aphanizomenon flose-aquae-related to modulation of CXCR4 expression by an L-selectin ligand? Cardiovascular Revascularization Medicine 2007 8, 189-202.

Kollet O., Spiegel A., Peled A., Petit I., Byk T., Hershkoviz R., Guetta E., Barkai G., Nagler A., Lapidot T., Rapid and efficient homing of human CD34(+)CD38(-/low)CXCR4 (+) stem and progenitor cells to the bone marrow and spleen of NOD/SCID and NOD/SCID/B2m(null) mice. Blood 2001 97, 3283-91.

Krause D., Theise N., Collector M., Henegariu O., Hwang S., Gardner R., Neutzel S., and Sharkis S., Multi-organ, multi-lineage engraftment by a single bone marrow-derived stem cell Cell 2001 105, 369-377

Kuang S, Gillespie M., Rudnicki M. Niche regulation of muscle satellite cell self-renewal and differentiation. Cell Stem Cell 2008 10, 22-31.

McCune J., Namikawa R., Kaneshima H., Shultz L., Lieberman M., Weissman I., The SCID-hu mouse: murine model for the analysis of human hematolymphoid differentiation and function. Science 1998, 241, 1632-9.

Mourão, P., and Pereira, M., Searching for alternatives to heparin: sulfated fucans from marine invertebrates. Trends in Cardiovascular Medicine 1999 9, 225-232.

Park H, Zhanga N., Park D., Topical application of *polygonum multiflorum* extract induces hair growth of resting hair follicles through upregulating Shh and β-catenin expression in C57BL/6 mice. Journal of Ethnopharmacology. 2011 May 17; 135(2):369-75. Epub 2011 Mar. 17.

Pereira M., Melo F., and Mourão, P., Is there a correlation between structure and anticoagulant action of sulfated galactans and sulfated fucans? Glycobiology 2002 12, 573-580.

Ren X L, Wang G F, Wang M, Ou-Yang H Z, Qi A D. Kinetics and mechanism of 2,3,5,4'-tetrahydroxystilbene-2-O-β-d-glycoside (THSG) degradation in aqueous solutions. J Pharm Biomed Anal. 2011 Apr. 28; 55(1):211-5. Epub 2010 Dec. 31.

Revishchin A., Korochkin L., Okhotin V., Pavlova G. Neural stem cells in the mammalian brain. International Review Cytology. 2008 265, 55-109.

Sweeney E., Priestly G., Nakamoto B., Collins R., and Beaudet A., Mobilization of stem/progenitor cells by sulfated polysaccharides does not require selectin presence. Proceedings of the National Academy of Sciences 2000 97, 6544-6549.

Sweeney E., Lortat-Jacob H., Priestly G., Nakamoto B. and Papayannopoulou T., Sulfated polysaccharides increase plasma levels of SDF-1 in monkeys and mice: involvement in mobilization of stem/progenitor cells. Blood 2008 99, 44-51.

Wang X., Foster M., Al-Dhalimy M., Lagasse E., Finegold M., and Grompe M., The origin and liver repopulating capacity of murine oval cells. Proceedings of the National Academy of Science 2003 Suppl. 1:11881-11888.

Yang L., Sun H., Sun T. and Qi N., The research progress of MSCs proliferation and differentiation in bone injury according to the TCM theory. African Journal of Biotechnology 2009 8: 524-528, 18 Feb., 2009

Yang L., Li S., Hatch H., Ahrens K., Cornelius J., Petersen B., Peck A. In vitro trans-differentiation of adult hepatic stem cells into pancreatic endocrine hormone-producing cells. Proceedings of the National Academy of Science 2002 99, 8078-83.

Zhou Z., Zhou J., Xing S., Effects of *polygonum multiflorum* extract on murine hematopoietic functions. Pharmacology and Clinics of Chinese Materia Medica 1991-05

The invention claimed is:

1. A method of increasing stem cell mobilization in a human in need thereof consisting essentially of:
administering a therapeutically effective amount of an extract of *Polygonum multiforum*, an extract of *Cordyceps Sinensis* and isolated fucoidan to said human in need thereof in an amount sufficient to increase stem cell mobilization in the human in need thereof wherein the stem cell mobilization is increased in the human in need thereof.

2. The method of claim 1, wherein the stem cell is a bone marrow-derived stem cell.

3. The method of claim 1, wherein the stem cell is a hematopoietic stem cell.

4. The method of claim 1, wherein the administering is via an oral administration.

5. The method of claim 4, wherein the oral administration is via a capsule or a pill.

6. The method of claim 1, wherein the therapeutically effective amount of an extract of *Polygonum multiforum*, is 10-2000 mg in a single dose.

7. The method of claim 1, wherein the therapeutically effective amount of isolated fucoidan is 10-2000 mg in a single dose.

8. The method of claim 1, wherein the therapeutically effective amount of an extract of *Cordyceps Sinensis* is 10-1000 mg in a single dose.

9. The method of claim 1, wherein the therapeutically effective amount of an extract of *Polygonum multiforum* is 10-2000 mg in a single dose, the therapeutically effective amount of isolated fucoidan is 10-2000 mg in a single dose and the therapeutically effective amount of an extract of *Cordyceps Sinensis* is 10-1000 mg in a single dose.

* * * * *